United States Patent
Muramatsu et al.

(10) Patent No.: US 10,894,967 B2
(45) Date of Patent: Jan. 19, 2021

(54) ALDEHYDE SYNTHASE GENE, RECOMBINANT MICROORGANISM COMPRISING THE SAME, AND METHOD FOR PRODUCING ALKANE USING THE SAME

(71) Applicants: Masayoshi Muramatsu, Miyoshi (JP); Shusei Obata, Nagoya (JP); Masakazu Ito, Toyota (JP); Jun Ogawa, Kyoto (JP); Shigenobu Kishino, Kyoto (JP)

(72) Inventors: Masayoshi Muramatsu, Miyoshi (JP); Shusei Obata, Nagoya (JP); Masakazu Ito, Toyota (JP); Jun Ogawa, Kyoto (JP); Shigenobu Kishino, Kyoto (JP)

(73) Assignees: Toyota Jidosha Kabushiki Kaisha, Toyota (JP); Kyoto University, Kyoto (JP)

( * ) Notice: Subject to any disclaimer, the term of this patent is extended or adjusted under 35 U.S.C. 154(b) by 0 days.

(21) Appl. No.: 16/807,495

(22) Filed: Mar. 3, 2020

(65) Prior Publication Data
US 2020/0283804 A1 Sep. 10, 2020

(30) Foreign Application Priority Data
Mar. 4, 2019 (JP) .................. 2019-038198

(51) Int. Cl.
C12N 9/02 (2006.01)
C12P 5/02 (2006.01)
C12R 1/19 (2006.01)
C12R 1/22 (2006.01)

(52) U.S. Cl.
CPC .............. *C12P 5/02* (2013.01); *C12N 9/0008* (2013.01); *C12R 1/19* (2013.01); *C12R 1/22* (2013.01)

(58) Field of Classification Search
CPC .................. C12P 5/02; C12N 9/0008
See application file for complete search history.

(56) References Cited

U.S. PATENT DOCUMENTS 8,846,371 B2  9/2014  Schirmer et al.

FOREIGN PATENT DOCUMENTS

JP   H07313153 A   12/1995

OTHER PUBLICATIONS

Yasufumi Yoshimoto et al, Applied Technology of Vegetable Oils for Diesel Engines—Use of Biodiesel Fuel-, Journal of the Combustion Society of Japan, 2009, vol. 156, p. 121-128.

I.J. Park, et al, "Corrosion characteristics of aluminum alloy in bio-ethanol blended gasoline fuel: Part 2. The effects of dissolved oxygen in the fuel," Fuel 90 (2011), p. 633-639.

Yu-Sin-Jang et al, "Engineering of microorganisms for the production of biofuels and perspectives based on systems metabolic engineering approaches", Biotechnology Advances 30, 2012, p. 989-1000.

Fengming Lin et al, "Aldehyde-forming fatty acyl-CoA reductase from cyanobacteria: expression, purification and characterization of the recombinant enzyme", the FEBS Journal, 280, p. 4773-4781, 2013.

Carl Andre et al, "Fusing catalase to an alkane-producing enzyme maintains enzymatic activity by converting the inhibitory byproduct H2O2 to the consubstrate O2", PNAS, vol. 110, No. 8, Feb. 19, 2013, p. 3191-3196.

Aditya M. Kunjapur et al, "Microbial Engineering for Aldehyde Synthesis", Applied and Environmental Microbiology, Mar. 2015, vol. 81, No. 6, p. 1892-1901.

Zia Fatma et al, "Identification of long chain specific aldehyde reductase and its use in enhanced fatty alcohol production in *E. coli*", Metabolic Engineering, vol. 37, 2016, p. 35-45.

*Primary Examiner* — Maryam Monshipouri
(74) *Attorney, Agent, or Firm* — Dinsmore & Shohl LLP

(57) ABSTRACT

The present disclosure provides a novel aldehyde synthase gene having activity of synthesizing a medium-chain aldehyde. Such gene encodes a protein comprising the amino acid sequence as shown in SEQ ID NO: 2.

20 Claims, 5 Drawing Sheets

Specification includes a Sequence Listing.

SEQUENCE LISTING

```
<160> NUMBER OF SEQ ID NOS: 13

<210> SEQ ID NO 1
<211> LENGTH: 1041
<212> TYPE: DNA
<213> ORGANISM: Pantoea sp.
<220> FEATURE:
<221> NAME/KEY: CDS
<222> LOCATION: (1)..(1041)

<400> SEQUENCE: 1 atg aac atg aag atc aaa acc acg atg aaa gcg gca gtt gtg aaa tcg      48
Met Asn Met Lys Ile Lys Thr Thr Met Lys Ala Ala Val Val Lys Ser
1               5                  10                   15 ttc ggt gag cct ttg gtg att gaa gaa gta ccg gtg cct tcg gtc ggg      96
Phe Gly Glu Pro Leu Val Ile Glu Glu Val Pro Val Pro Ser Val Gly
                20                  25                   30 ccg ggt cag gtt ttg gta aaa att gcc gcc acc ggg gtt tgc cat acc     144
Pro Gly Gln Val Leu Val Lys Ile Ala Ala Thr Gly Val Cys His Thr
            35                  40                   45 gat ttg cac gct gct gaa ggt gac tgg ccg atc aaa cct aat ccc ccc     192
Asp Leu His Ala Ala Glu Gly Asp Trp Pro Ile Lys Pro Asn Pro Pro
        50                  55                   60 ttt att ccc ggc cat gaa ggt gtt ggt cag gtt gtg gcg ctg ggc gaa     240
Phe Ile Pro Gly His Glu Gly Val Gly Gln Val Val Ala Leu Gly Glu
65                  70                  75                   80 ggt gtg aaa cat ctc aaa ctt ggc gat cgc gtg ggt gtg ccc tgg ctc     288
Gly Val Lys His Leu Lys Leu Gly Asp Arg Val Gly Val Pro Trp Leu
                85                  90                   95 tac tcg gcc tgt ggt cat tgc gaa tat tgt ctc gat agc tgg gaa acg     336
Tyr Ser Ala Cys Gly His Cys Glu Tyr Cys Leu Asp Ser Trp Glu Thr
                100                 105                  110
```

| | | |
|---|---|---|
| ctg tgt ctg tcg cag cag aat gcc ggt tat tca gtc aat ggt agc ttt<br>Leu Cys Leu Ser Gln Gln Asn Ala Gly Tyr Ser Val Asn Gly Ser Phe<br>115                       120                     125 | 384 | |
| gca gag tat tgc ctg gcg gat gct aac tac gtc ggt atc ctg ccg gat<br>Ala Glu Tyr Cys Leu Ala Asp Ala Asn Tyr Val Gly Ile Leu Pro Asp<br>130                       135                     140 | 432 | |
| aat att gag tat cat gag atc gca ccg att ttg tgt gcc ggt gtc acg<br>Asn Ile Glu Tyr His Glu Ile Ala Pro Ile Leu Cys Ala Gly Val Thr<br>145                       150                     155                     160 | 480 | |
| gtg tac aaa ggg ctg aag atg acc gat acc aag cca ggt gac tgg gtg<br>Val Tyr Lys Gly Leu Lys Met Thr Asp Thr Lys Pro Gly Asp Trp Val<br>                     165                     170                     175 | 528 | |
| gtg att tcc ggt atc ggt ggt ttg gga cat atg gct gtt cag tac gcg<br>Val Ile Ser Gly Ile Gly Gly Leu Gly His Met Ala Val Gln Tyr Ala<br>                  180                     185                     190 | 576 | |
| gta gcg atg ggg ctt aac gtg gct gct gtt gat att gat gac gag aag<br>Val Ala Met Gly Leu Asn Val Ala Ala Val Asp Ile Asp Asp Glu Lys<br>                195                     200                     205 | 624 | |
| ctg gag ttt gct aaa cgt ctg ggt gcc agc gtg gtg gct aac gcg aaa<br>Leu Glu Phe Ala Lys Arg Leu Gly Ala Ser Val Val Ala Asn Ala Lys<br>210                       215                     220 | 672 | |
| aat gtc gat ccg gcg aaa ttc ttc cac gaa agc ttc ggc ggc gcg cac<br>Asn Val Asp Pro Ala Lys Phe Phe His Glu Ser Phe Gly Gly Ala His<br>225                       230                     235                     240 | 720 | |
| ggt gtg ctg gtg aca gcg gtt tca ccg aaa gcc ttt gag caa gcg ttg<br>Gly Val Leu Val Thr Ala Val Ser Pro Lys Ala Phe Glu Gln Ala Leu<br>                       245                     250                     255 | 768 | |
| gga acc atg cgt cgt ggc ggt acg atg gtg ctg aat ggc ctg ccg ccg<br>Gly Thr Met Arg Arg Gly Gly Thr Met Val Leu Asn Gly Leu Pro Pro<br>                   260                     265                     270 | 816 | |
| ggc aaa ttt gac ctg tcg att ttt gac atg gtg ttg gac ggt att acg<br>Gly Lys Phe Asp Leu Ser Ile Phe Asp Met Val Leu Asp Gly Ile Thr<br>                       275                     280                     285 | 864 | |
| gtg cgc ggt tca att gtc ggc acc cgt aag gat ttg cag gag gcg ctc<br>Val Arg Gly Ser Ile Val Gly Thr Arg Lys Asp Leu Gln Glu Ala Leu<br>                290                     295                     300 | 912 | |
| gac ttc gct ggt cgt cac aaa gtg aaa gcc aat gta gcg gtg gag ccg<br>Asp Phe Ala Gly Arg His Lys Val Lys Ala Asn Val Ala Val Glu Pro<br>305                       310                     315                     320 | 960 | |
| ttg gtc aac atc aac gat atc ttt gcc cgc atg cat gcc ggt aaa att<br>Leu Val Asn Ile Asn Asp Ile Phe Ala Arg Met His Ala Gly Lys Ile<br>                       325                     330                     335 | 1008 | |
| gaa ggc cgt att gtt gtt gat atg tcg ctg taa<br>Glu Gly Arg Ile Val Val Asp Met Ser Leu<br>340                       345 | 1041 | |

<210> SEQ ID NO 2
<211> LENGTH: 346
<212> TYPE: PRT
<213> ORGANISM: Pantoea sp.

<400> SEQUENCE: 2

Met Asn Met Lys Ile Lys Thr Thr Met Lys Ala Ala Val Val Lys Ser
1                  5                    10                  15

Phe Gly Glu Pro Leu Val Ile Glu Glu Val Pro Val Pro Ser Val Gly
                 20                    25                  30

Pro Gly Gln Val Leu Val Lys Ile Ala Ala Thr Gly Val Cys His Thr
              35                    40                  45

Asp Leu His Ala Ala Glu Gly Asp Trp Pro Ile Lys Pro Asn Pro Pro
  50                    55                    60

Phe Ile Pro Gly His Glu Gly Val Gly Gln Val Val Ala Leu Gly Glu
65                  70                  75                  80

Gly Val Lys His Leu Lys Leu Gly Asp Arg Val Gly Val Pro Trp Leu
            85                  90                  95

Tyr Ser Ala Cys Gly His Cys Glu Tyr Cys Leu Asp Ser Trp Glu Thr
        100                 105                 110

Leu Cys Leu Ser Gln Gln Asn Ala Gly Tyr Ser Val Asn Gly Ser Phe
    115                 120                 125

Ala Glu Tyr Cys Leu Ala Asp Ala Asn Tyr Val Gly Ile Leu Pro Asp
130                 135                 140

Asn Ile Glu Tyr His Glu Ile Ala Pro Ile Leu Cys Ala Gly Val Thr
145                 150                 155                 160

Val Tyr Lys Gly Leu Lys Met Thr Asp Thr Lys Pro Gly Asp Trp Val
            165                 170                 175

Val Ile Ser Gly Ile Gly Gly Leu Gly His Met Ala Val Gln Tyr Ala
        180                 185                 190

Val Ala Met Gly Leu Asn Val Ala Ala Val Asp Ile Asp Asp Glu Lys
    195                 200                 205

Leu Glu Phe Ala Lys Arg Leu Gly Ala Ser Val Ala Asn Ala Lys
210                 215                 220

Asn Val Asp Pro Ala Lys Phe Phe His Glu Ser Phe Gly Gly Ala His
225                 230                 235                 240

Gly Val Leu Val Thr Ala Val Ser Pro Lys Ala Phe Glu Gln Ala Leu
            245                 250                 255

Gly Thr Met Arg Arg Gly Gly Thr Met Val Leu Asn Gly Leu Pro Pro
        260                 265                 270

Gly Lys Phe Asp Leu Ser Ile Phe Asp Met Val Leu Asp Gly Ile Thr
    275                 280                 285

Val Arg Gly Ser Ile Val Gly Thr Arg Lys Asp Leu Gln Glu Ala Leu
290                 295                 300

Asp Phe Ala Gly Arg His Lys Val Lys Ala Asn Val Ala Val Glu Pro
305                 310                 315                 320

Leu Val Asn Ile Asn Asp Ile Phe Ala Arg Met His Ala Gly Lys Ile
            325                 330                 335

Glu Gly Arg Ile Val Val Asp Met Ser Leu
        340                 345

<210> SEQ ID NO 3
<211> LENGTH: 20
<212> TYPE: PRT
<213> ORGANISM: Pantoea sp.

<400> SEQUENCE: 3

Met Asn Met Lys Ile Lys Thr Thr Met Lys Ala Ala Val Val Lys Ser
1               5                   10                  15

Phe Gly Glu Pro
            20

<210> SEQ ID NO 4
<211> LENGTH: 699
<212> TYPE: DNA
<213> ORGANISM: Nostoc punctiforme PCC73102
<220> FEATURE:
<221> NAME/KEY: CDS
<222> LOCATION: (1)..(699)

<400> SEQUENCE: 4

```
atg cag cag ctt aca gac caa tct aaa gaa tta gat ttc aag agc gaa      48
Met Gln Gln Leu Thr Asp Gln Ser Lys Glu Leu Asp Phe Lys Ser Glu
1               5                   10                  15 aca tac aaa gat gct tat agc cgg att aat gcg atc gtg att gaa ggg      96
Thr Tyr Lys Asp Ala Tyr Ser Arg Ile Asn Ala Ile Val Ile Glu Gly
                20                  25                  30 gaa caa gaa gcc cat gaa aat tac atc aca cta gcc caa ctg ctg cca     144
Glu Gln Glu Ala His Glu Asn Tyr Ile Thr Leu Ala Gln Leu Leu Pro
            35                  40                  45 gaa tct cat gat gaa ttg att cgc cta tcc aag atg gaa agc cgc cat     192
Glu Ser His Asp Glu Leu Ile Arg Leu Ser Lys Met Glu Ser Arg His
        50                  55                  60 aag aaa gga ttt gaa gct tgt ggg cgc aat tta gct gtt acc cca gat     240
Lys Lys Gly Phe Glu Ala Cys Gly Arg Asn Leu Ala Val Thr Pro Asp
65                  70                  75                  80 ttg caa ttt gcc aaa gag ttt ttc tcc ggc cta cac caa aat ttt caa     288
Leu Gln Phe Ala Lys Glu Phe Phe Ser Gly Leu His Gln Asn Phe Gln
                85                  90                  95 aca gct gcc gca gaa ggg aaa gtg gtt act tgt ctg ttg att cag tct     336
Thr Ala Ala Ala Glu Gly Lys Val Val Thr Cys Leu Leu Ile Gln Ser
                100                 105                 110 tta att att gaa tgt ttt gcg atc gca gca tat aac att tac atc ccc     384
Leu Ile Ile Glu Cys Phe Ala Ile Ala Ala Tyr Asn Ile Tyr Ile Pro
            115                 120                 125 gtt gcc gac gat ttc gcc cgt aaa att act gaa gga gta gtt aaa gaa     432
Val Ala Asp Asp Phe Ala Arg Lys Ile Thr Glu Gly Val Val Lys Glu
        130                 135                 140 gaa tac agc cac ctc aat ttt gga gaa gtt tgg ttg aaa gaa cac ttt     480
Glu Tyr Ser His Leu Asn Phe Gly Glu Val Trp Leu Lys Glu His Phe
145                 150                 155                 160 gca gaa tcc aaa gct gaa ctt gaa ctt gca aat cgc cag aac cta ccc     528
Ala Glu Ser Lys Ala Glu Leu Glu Leu Ala Asn Arg Gln Asn Leu Pro
                165                 170                 175 atc gtc tgg aaa atg ctc aac caa gta gaa ggt gat gcc cac aca atg     576
Ile Val Trp Lys Met Leu Asn Gln Val Glu Gly Asp Ala His Thr Met
                180                 185                 190 gca atg gaa aaa gat gct ttg gta gaa gac ttc atg att cag tat ggt     624
Ala Met Glu Lys Asp Ala Leu Val Glu Asp Phe Met Ile Gln Tyr Gly
            195                 200                 205 gaa gca ttg agt aac att ggt ttt tcg act cgc gat att atg cgc ttg     672
Glu Ala Leu Ser Asn Ile Gly Phe Ser Thr Arg Asp Ile Met Arg Leu
        210                 215                 220 tca gcc tac gga ctc ata ggt gct taa                                 699
Ser Ala Tyr Gly Leu Ile Gly Ala
225                 230

<210> SEQ ID NO 5
<211> LENGTH: 232
<212> TYPE: PRT
<213> ORGANISM: Nostoc punctiforme PCC73102

<400> SEQUENCE: 5

Met Gln Gln Leu Thr Asp Gln Ser Lys Glu Leu Asp Phe Lys Ser Glu
1               5                   10                  15

Thr Tyr Lys Asp Ala Tyr Ser Arg Ile Asn Ala Ile Val Ile Glu Gly
                20                  25                  30

Glu Gln Glu Ala His Glu Asn Tyr Ile Thr Leu Ala Gln Leu Leu Pro
            35                  40                  45

Glu Ser His Asp Glu Leu Ile Arg Leu Ser Lys Met Glu Ser Arg His
```

```
                    50                  55                  60
Lys Lys Gly Phe Glu Ala Cys Gly Arg Asn Leu Ala Val Thr Pro Asp
 65                  70                  75                  80

Leu Gln Phe Ala Lys Glu Phe Phe Ser Gly Leu His Gln Asn Phe Gln
                 85                  90                  95

Thr Ala Ala Ala Glu Gly Lys Val Val Thr Cys Leu Leu Ile Gln Ser
            100                 105                 110

Leu Ile Ile Glu Cys Phe Ala Ile Ala Ala Tyr Asn Ile Tyr Ile Pro
        115                 120                 125

Val Ala Asp Asp Phe Ala Arg Lys Ile Thr Glu Gly Val Val Lys Glu
    130                 135                 140

Glu Tyr Ser His Leu Asn Phe Gly Glu Val Trp Leu Lys Glu His Phe
145                 150                 155                 160

Ala Glu Ser Lys Ala Glu Leu Glu Leu Ala Asn Arg Gln Asn Leu Pro
                165                 170                 175

Ile Val Trp Lys Met Leu Asn Gln Val Glu Gly Asp Ala His Thr Met
            180                 185                 190

Ala Met Glu Lys Asp Ala Leu Val Glu Asp Phe Met Ile Gln Tyr Gly
        195                 200                 205

Glu Ala Leu Ser Asn Ile Gly Phe Ser Thr Arg Asp Ile Met Arg Leu
    210                 215                 220

Ser Ala Tyr Gly Leu Ile Gly Ala
225                 230

<210> SEQ ID NO 6
<211> LENGTH: 324
<212> TYPE: DNA
<213> ORGANISM: Nostoc punctiforme PCC73102
<220> FEATURE:
<221> NAME/KEY: CDS
<222> LOCATION: (1)..(324)

<400> SEQUENCE: 6 atg gaa ccg aaa acc tat acc gtg gaa att gat cat cag ggc aaa atc      48
Met Glu Pro Lys Thr Tyr Thr Val Glu Ile Asp His Gln Gly Lys Ile
  1               5                  10                  15 cat acc ctg cag gtg ccg gaa aac gaa acc att ctg agc gtt gcc gat      96
His Thr Leu Gln Val Pro Glu Asn Glu Thr Ile Leu Ser Val Ala Asp
                 20                  25                  30 gcc gcg ggc ctg gaa ctg ccg agc agc tgc aat gcg ggt gtt tgc acc     144
Ala Ala Gly Leu Glu Leu Pro Ser Ser Cys Asn Ala Gly Val Cys Thr
             35                  40                  45 acc tgt gcc ggc cag atc agc cag ggt acc gtg gat cag acc gat ggc     192
Thr Cys Ala Gly Gln Ile Ser Gln Gly Thr Val Asp Gln Thr Asp Gly
         50                  55                  60 atg ggt gtt agc ccg gat ctg cag aaa cag ggc tat gtg ctg ctg tgt     240
Met Gly Val Ser Pro Asp Leu Gln Lys Gln Gly Tyr Val Leu Leu Cys
 65                  70                  75                  80 gtt gcc aaa ccg ctg agc gat ctg aaa ctg gaa acc gaa aaa gaa gat     288
Val Ala Lys Pro Leu Ser Asp Leu Lys Leu Glu Thr Glu Lys Glu Asp
                 85                  90                  95 att gtg tat cag ctg cag ttt ggt aaa gat aaa taa                    324
Ile Val Tyr Gln Leu Gln Phe Gly Lys Asp Lys
            100                 105

<210> SEQ ID NO 7
<211> LENGTH: 107
<212> TYPE: PRT
<213> ORGANISM: Nostoc punctiforme PCC73102
```

<400> SEQUENCE: 7

| Met | Glu | Pro | Lys | Thr | Tyr | Thr | Val | Glu | Ile | Asp | His | Gln | Gly | Lys | Ile |
|---|---|---|---|---|---|---|---|---|---|---|---|---|---|---|---|
| 1 | | | | 5 | | | | | 10 | | | | | 15 | |

| His | Thr | Leu | Gln | Val | Pro | Glu | Asn | Glu | Thr | Ile | Leu | Ser | Val | Ala | Asp |
|---|---|---|---|---|---|---|---|---|---|---|---|---|---|---|---|
| | | | 20 | | | | | 25 | | | | | 30 | | |

| Ala | Ala | Gly | Leu | Glu | Leu | Pro | Ser | Ser | Cys | Asn | Ala | Gly | Val | Cys | Thr |
|---|---|---|---|---|---|---|---|---|---|---|---|---|---|---|---|
| | | | 35 | | | | | 40 | | | | | 45 | | |

| Thr | Cys | Ala | Gly | Gln | Ile | Ser | Gln | Gly | Thr | Val | Asp | Gln | Thr | Asp | Gly |
|---|---|---|---|---|---|---|---|---|---|---|---|---|---|---|---|
| | 50 | | | | | 55 | | | | | 60 | | | | |

| Met | Gly | Val | Ser | Pro | Asp | Leu | Gln | Lys | Gln | Gly | Tyr | Val | Leu | Leu | Cys |
|---|---|---|---|---|---|---|---|---|---|---|---|---|---|---|---|
| 65 | | | | | 70 | | | | | 75 | | | | | 80 |

| Val | Ala | Lys | Pro | Leu | Ser | Asp | Leu | Lys | Leu | Glu | Thr | Glu | Lys | Glu | Asp |
|---|---|---|---|---|---|---|---|---|---|---|---|---|---|---|---|
| | | | | 85 | | | | | 90 | | | | | 95 | |

| Ile | Val | Tyr | Gln | Leu | Gln | Phe | Gly | Lys | Asp | Lys |
|---|---|---|---|---|---|---|---|---|---|---|
| | | | 100 | | | | | 105 | | |

<210> SEQ ID NO 8
<211> LENGTH: 1317
<212> TYPE: DNA
<213> ORGANISM: Nostoc punctiforme PCC73102
<220> FEATURE:
<221> NAME/KEY: CDS
<222> LOCATION: (1)..(1317)

<400> SEQUENCE: 8

```
atg gaa tat aat cag ggt gcc gtg gaa ggt gcc gcg aac att gaa ctg     48
Met Glu Tyr Asn Gln Gly Ala Val Glu Gly Ala Ala Asn Ile Glu Leu
1               5                   10                  15 ggt agc cgt att ttt gtc tat gaa gtg gtc ggt ctg cgt cag ggt gaa     96
Gly Ser Arg Ile Phe Val Tyr Glu Val Val Gly Leu Arg Gln Gly Glu
            20                  25                  30 gaa acc gat cag acc aac tat ccg atc cgt aaa agc ggc agc gtg ttt    144
Glu Thr Asp Gln Thr Asn Tyr Pro Ile Arg Lys Ser Gly Ser Val Phe
        35                  40                  45 att cgt gtt ccg tat aac cgc atg aat cag gaa atg cgt cgc att acc    192
Ile Arg Val Pro Tyr Asn Arg Met Asn Gln Glu Met Arg Arg Ile Thr
    50                  55                  60 cgc ctg ggc ggt acc att gtg agc atc cag ccg att acc gcg ctg gaa    240
Arg Leu Gly Gly Thr Ile Val Ser Ile Gln Pro Ile Thr Ala Leu Glu
65                  70                  75                  80 ccg gtt aac ggc aaa gcg agc ttt ggt aat gcc acc agc gtg gtt agc    288
Pro Val Asn Gly Lys Ala Ser Phe Gly Asn Ala Thr Ser Val Val Ser
                85                  90                  95 gaa ctg gcg aaa agc ggt gaa acc gcc aac agc gaa ggc aat ggt aaa    336
Glu Leu Ala Lys Ser Gly Glu Thr Ala Asn Ser Glu Gly Asn Gly Lys
            100                 105                 110 gcc acc ccg gtg aat gcg cat agc gcc gaa gaa cag aac aaa gat aag    384
Ala Thr Pro Val Asn Ala His Ser Ala Glu Glu Gln Asn Lys Asp Lys
        115                 120                 125 aaa ggc aat acc atg acc cag gcg aaa gcg aag aaa gat cat ggc gat    432
Lys Gly Asn Thr Met Thr Gln Ala Lys Ala Lys Lys Asp His Gly Asp
    130                 135                 140 gtg ccg gtt aac acc tat cgt ccg aat gcg ccg ttt atc ggc aaa gtg    480
Val Pro Val Asn Thr Tyr Arg Pro Asn Ala Pro Phe Ile Gly Lys Val
145                 150                 155                 160 att agc aac gaa ccg ctg gtt aaa gaa ggc ggt att ggt atc gtg cag    528
Ile Ser Asn Glu Pro Leu Val Lys Glu Gly Gly Ile Gly Ile Val Gln
                165                 170                 175
```

| | | | | | | | | | | | | | | | | |
|---|---|---|---|---|---|---|---|---|---|---|---|---|---|---|---|---|
| cat | ctg | aaa | ttt | gat | ctg | agc | ggc | ggt | gat | ctg | aaa | tat | atc | gaa | ggc | 576 |
| His | Leu | Lys | Phe | Asp | Leu | Ser | Gly | Gly | Asp | Leu | Lys | Tyr | Ile | Glu | Gly | |
| | | | | 180 | | | | | 185 | | | | | 190 | | |
| cag | agc | att | ggt | att | atc | ccg | ccg | ggc | ctg | gat | aaa | aat | ggt | aaa | ccg | 624 |
| Gln | Ser | Ile | Gly | Ile | Ile | Pro | Pro | Gly | Leu | Asp | Lys | Asn | Gly | Lys | Pro | |
| | | 195 | | | | | 200 | | | | | 205 | | | | |
| gaa | aaa | ctg | cgt | ctg | tat | agc | att | gcg | agc | acc | cgt | cat | ggc | gat | gat | 672 |
| Glu | Lys | Leu | Arg | Leu | Tyr | Ser | Ile | Ala | Ser | Thr | Arg | His | Gly | Asp | Asp | |
| 210 | | | | | 215 | | | | | 220 | | | | | | |
| gtt | gat | gat | aaa | acc | gtg | agc | ctg | tgc | gtt | cgt | cag | ctg | gaa | tat | aaa | 720 |
| Val | Asp | Asp | Lys | Thr | Val | Ser | Leu | Cys | Val | Arg | Gln | Leu | Glu | Tyr | Lys | |
| 225 | | | | 230 | | | | | 235 | | | | | 240 | | |
| cat | ccg | gaa | acc | ggc | gaa | acc | gtg | tat | ggt | gtt | tgc | agc | acc | cat | ctg | 768 |
| His | Pro | Glu | Thr | Gly | Glu | Thr | Val | Tyr | Gly | Val | Cys | Ser | Thr | His | Leu | |
| | | | | 245 | | | | | 250 | | | | | 255 | | |
| tgt | ttt | ctg | aaa | ccg | ggt | gaa | gaa | gtg | aaa | atc | acc | ggc | ccg | gtt | ggt | 816 |
| Cys | Phe | Leu | Lys | Pro | Gly | Glu | Glu | Val | Lys | Ile | Thr | Gly | Pro | Val | Gly | |
| | | 260 | | | | | 265 | | | | | 270 | | | | |
| aaa | gaa | atg | ctg | ctg | ccg | aac | gat | ccg | gat | gcg | aat | gtg | atc | atg | atg | 864 |
| Lys | Glu | Met | Leu | Leu | Pro | Asn | Asp | Pro | Asp | Ala | Asn | Val | Ile | Met | Met | |
| 275 | | | | | 280 | | | | | 285 | | | | | | |
| gca | acc | ggt | acc | ggt | att | gcc | ccg | atg | cgt | gcc | tat | ctg | tgg | cgc | cag | 912 |
| Ala | Thr | Gly | Thr | Gly | Ile | Ala | Pro | Met | Arg | Ala | Tyr | Leu | Trp | Arg | Gln | |
| | 290 | | | | | 295 | | | | | 300 | | | | | |
| ttt | aaa | gat | gcg | gaa | cgc | gcg | gcc | aac | ccg | gaa | tat | cag | ttt | aaa | ggc | 960 |
| Phe | Lys | Asp | Ala | Glu | Arg | Ala | Ala | Asn | Pro | Glu | Tyr | Gln | Phe | Lys | Gly | |
| 305 | | | | | 310 | | | | | 315 | | | | | 320 | |
| ttt | agc | tgg | ctg | att | ttt | ggt | gtt | ccg | acc | acc | ccg | aat | ctg | ctg | tat | 1008 |
| Phe | Ser | Trp | Leu | Ile | Phe | Gly | Val | Pro | Thr | Thr | Pro | Asn | Leu | Leu | Tyr | |
| | | | 325 | | | | | 330 | | | | | 335 | | | |
| aaa | gaa | gaa | ctg | gaa | gaa | atc | cag | cag | aaa | tat | ccg | gaa | aac | ttt | cgt | 1056 |
| Lys | Glu | Glu | Leu | Glu | Glu | Ile | Gln | Gln | Lys | Tyr | Pro | Glu | Asn | Phe | Arg | |
| | | | 340 | | | | | 345 | | | | | 350 | | | |
| ctg | acc | gcg | gcc | att | agc | cgc | gaa | cag | aaa | aat | ccg | cag | ggc | ggt | cgt | 1104 |
| Leu | Thr | Ala | Ala | Ile | Ser | Arg | Glu | Gln | Lys | Asn | Pro | Gln | Gly | Gly | Arg | |
| | | 355 | | | | | 360 | | | | | 365 | | | | |
| atg | tat | atc | cag | gat | cgc | gtg | gcg | gaa | cat | gcc | gat | gaa | ctg | tgg | cag | 1152 |
| Met | Tyr | Ile | Gln | Asp | Arg | Val | Ala | Glu | His | Ala | Asp | Glu | Leu | Trp | Gln | |
| 370 | | | | | 375 | | | | | 380 | | | | | | |
| ctg | atc | aaa | aac | gaa | aaa | acc | cat | acc | tat | att | tgt | ggc | ctg | cgc | ggt | 1200 |
| Leu | Ile | Lys | Asn | Glu | Lys | Thr | His | Thr | Tyr | Ile | Cys | Gly | Leu | Arg | Gly | |
| 385 | | | | 390 | | | | | 395 | | | | | 400 | | |
| atg | gaa | gaa | ggc | att | gat | gcc | gca | ctg | acc | gcg | gcg | gcg | gca | aaa | gaa | 1248 |
| Met | Glu | Glu | Gly | Ile | Asp | Ala | Ala | Leu | Thr | Ala | Ala | Ala | Ala | Lys | Glu | |
| | | | | 405 | | | | | 410 | | | | | 415 | | |
| ggt | gtt | acc | tgg | tcg | gat | tat | caa | aaa | caa | ctg | aaa | aag | gct | ggt | cgt | 1296 |
| Gly | Val | Thr | Trp | Ser | Asp | Tyr | Gln | Lys | Gln | Leu | Lys | Lys | Ala | Gly | Arg | |
| | | 420 | | | | | 425 | | | | | 430 | | | | |
| tgg | cat | gtg | gaa | acc | tat | taa | | | | | | | | | | 1317 |
| Trp | His | Val | Glu | Thr | Tyr | | | | | | | | | | | |
| | | 435 | | | | | | | | | | | | | | |

<210> SEQ ID NO 9
<211> LENGTH: 438
<212> TYPE: PRT
<213> ORGANISM: Nostoc punctiforme PCC73102

<400> SEQUENCE: 9

| | | | | | | | | | | | | | | | |
|---|---|---|---|---|---|---|---|---|---|---|---|---|---|---|---|
| Met | Glu | Tyr | Asn | Gln | Gly | Ala | Val | Glu | Gly | Ala | Ala | Asn | Ile | Glu | Leu |
| 1 | | | | 5 | | | | | 10 | | | | | 15 | |

```
Gly Ser Arg Ile Phe Val Tyr Glu Val Val Gly Leu Arg Gln Gly Glu
            20                  25                  30

Glu Thr Asp Gln Thr Asn Tyr Pro Ile Arg Lys Ser Gly Ser Val Phe
         35                  40                  45

Ile Arg Val Pro Tyr Asn Arg Met Asn Gln Glu Met Arg Arg Ile Thr
 50                  55                  60

Arg Leu Gly Gly Thr Ile Val Ser Ile Gln Pro Ile Thr Ala Leu Glu
 65                  70                  75                  80

Pro Val Asn Gly Lys Ala Ser Phe Gly Asn Ala Thr Ser Val Val Ser
                 85                  90                  95

Glu Leu Ala Lys Ser Gly Glu Thr Ala Asn Ser Glu Gly Asn Gly Lys
                100                 105                 110

Ala Thr Pro Val Asn Ala His Ser Ala Glu Glu Gln Asn Lys Asp Lys
            115                 120                 125

Lys Gly Asn Thr Met Thr Gln Ala Lys Ala Lys Lys Asp His Gly Asp
        130                 135                 140

Val Pro Val Asn Thr Tyr Arg Pro Asn Ala Pro Phe Ile Gly Lys Val
145                 150                 155                 160

Ile Ser Asn Glu Pro Leu Val Lys Glu Gly Ile Gly Ile Val Gln
                165                 170                 175

His Leu Lys Phe Asp Leu Ser Gly Gly Asp Leu Lys Tyr Ile Glu Gly
            180                 185                 190

Gln Ser Ile Gly Ile Pro Pro Gly Leu Asp Lys Asn Gly Lys Pro
        195                 200                 205

Glu Lys Leu Arg Leu Tyr Ser Ile Ala Ser Thr Arg His Gly Asp Asp
    210                 215                 220

Val Asp Asp Lys Thr Val Ser Leu Cys Val Arg Gln Leu Glu Tyr Lys
225                 230                 235                 240

His Pro Glu Thr Gly Glu Thr Val Tyr Gly Val Cys Ser Thr His Leu
                245                 250                 255

Cys Phe Leu Lys Pro Gly Glu Glu Val Lys Ile Thr Gly Pro Val Gly
            260                 265                 270

Lys Glu Met Leu Leu Pro Asn Asp Pro Asp Ala Asn Val Ile Met Met
        275                 280                 285

Ala Thr Gly Thr Gly Ile Ala Pro Met Arg Ala Tyr Leu Trp Arg Gln
    290                 295                 300

Phe Lys Asp Ala Glu Arg Ala Ala Asn Pro Glu Tyr Gln Phe Lys Gly
305                 310                 315                 320

Phe Ser Trp Leu Ile Phe Gly Val Pro Thr Thr Pro Asn Leu Leu Tyr
                325                 330                 335

Lys Glu Glu Leu Glu Glu Ile Gln Gln Lys Tyr Pro Glu Asn Phe Arg
            340                 345                 350

Leu Thr Ala Ala Ile Ser Arg Glu Gln Lys Asn Pro Gln Gly Gly Arg
        355                 360                 365

Met Tyr Ile Gln Asp Arg Val Ala Glu His Ala Asp Glu Leu Trp Gln
    370                 375                 380

Leu Ile Lys Asn Glu Lys Thr His Thr Tyr Ile Cys Gly Leu Arg Gly
385                 390                 395                 400

Met Glu Glu Gly Ile Asp Ala Ala Leu Thr Ala Ala Ala Lys Glu
                405                 410                 415

Gly Val Thr Trp Ser Asp Tyr Gln Lys Gln Leu Lys Lys Ala Gly Arg
            420                 425                 430

Trp His Val Glu Thr Tyr
```

<210> SEQ ID NO 10
<211> LENGTH: 1026
<212> TYPE: DNA
<213> ORGANISM: Synechococcus elongatus PCC7942
<220> FEATURE:
<221> NAME/KEY: CDS
<222> LOCATION: (1)..(1026)

<400> SEQUENCE: 10

| | | | | | | | | | | | | | | | | |
|---|---|---|---|---|---|---|---|---|---|---|---|---|---|---|---|---|
| atg | ttc | ggt | ctt | atc | ggt | cat | ctc | acc | agt | ttg | gag | cag | gcc | cgc | gac | 48 |
| Met | Phe | Gly | Leu | Ile | Gly | His | Leu | Thr | Ser | Leu | Glu | Gln | Ala | Arg | Asp | |
| 1 | | | | 5 | | | | | 10 | | | | | 15 | | |
| gtt | tct | cgc | agg | atg | ggc | tac | gac | gaa | tac | gcc | gat | caa | gga | ttg | gag | 96 |
| Val | Ser | Arg | Arg | Met | Gly | Tyr | Asp | Glu | Tyr | Ala | Asp | Gln | Gly | Leu | Glu | |
| | | | 20 | | | | | 25 | | | | | 30 | | | |
| ttt | tgg | agt | agc | gct | cct | cct | caa | atc | gtt | gat | gaa | atc | aca | gtc | acc | 144 |
| Phe | Trp | Ser | Ser | Ala | Pro | Pro | Gln | Ile | Val | Asp | Glu | Ile | Thr | Val | Thr | |
| | | 35 | | | | | 40 | | | | | 45 | | | | |
| agt | gcc | aca | ggc | aag | gtg | att | cac | ggt | cgc | tac | atc | gaa | tcg | tgt | ttc | 192 |
| Ser | Ala | Thr | Gly | Lys | Val | Ile | His | Gly | Arg | Tyr | Ile | Glu | Ser | Cys | Phe | |
| 50 | | | | | 55 | | | | | 60 | | | | | | |
| ttg | ccg | gaa | atg | ctg | gcg | gcg | cgc | cgc | ttc | aaa | aca | gcc | acg | cgc | aaa | 240 |
| Leu | Pro | Glu | Met | Leu | Ala | Ala | Arg | Arg | Phe | Lys | Thr | Ala | Thr | Arg | Lys | |
| 65 | | | | | 70 | | | | | 75 | | | | | 80 | |
| gtt | ctc | aat | gcc | atg | tcc | cat | gcc | caa | aaa | cac | ggc | atc | gac | atc | tcg | 288 |
| Val | Leu | Asn | Ala | Met | Ser | His | Ala | Gln | Lys | His | Gly | Ile | Asp | Ile | Ser | |
| | | | | 85 | | | | | 90 | | | | | 95 | | |
| gcc | ttg | ggg | ggc | ttt | acc | tcg | att | att | ttc | gag | aat | ttc | gat | ttg | gcc | 336 |
| Ala | Leu | Gly | Gly | Phe | Thr | Ser | Ile | Ile | Phe | Glu | Asn | Phe | Asp | Leu | Ala | |
| | | | 100 | | | | | 105 | | | | | 110 | | | |
| agt | ttg | cgg | caa | gtg | cgc | gac | act | acc | ttg | gag | ttt | gaa | cgg | ttc | acc | 384 |
| Ser | Leu | Arg | Gln | Val | Arg | Asp | Thr | Thr | Leu | Glu | Phe | Glu | Arg | Phe | Thr | |
| | | 115 | | | | | 120 | | | | | 125 | | | | |
| acc | ggc | aat | act | cac | acg | gcc | tac | gta | atc | tgt | aga | cag | gtg | gaa | gcc | 432 |
| Thr | Gly | Asn | Thr | His | Thr | Ala | Tyr | Val | Ile | Cys | Arg | Gln | Val | Glu | Ala | |
| 130 | | | | | 135 | | | | | 140 | | | | | | |
| gct | gct | aaa | acg | ctg | ggc | atc | gac | att | acc | caa | gcg | aca | gta | gcg | gtt | 480 |
| Ala | Ala | Lys | Thr | Leu | Gly | Ile | Asp | Ile | Thr | Gln | Ala | Thr | Val | Ala | Val | |
| 145 | | | | | 150 | | | | | 155 | | | | | 160 | |
| gtc | ggc | gcg | act | ggc | gat | atc | ggt | agc | gct | gtc | tgc | cgc | tgg | ctc | gac | 528 |
| Val | Gly | Ala | Thr | Gly | Asp | Ile | Gly | Ser | Ala | Val | Cys | Arg | Trp | Leu | Asp | |
| | | | | 165 | | | | | 170 | | | | | 175 | | |
| ctc | aaa | ctg | ggt | gtc | ggt | gat | ttg | atc | ctg | acg | gcg | cgc | aat | cag | gag | 576 |
| Leu | Lys | Leu | Gly | Val | Gly | Asp | Leu | Ile | Leu | Thr | Ala | Arg | Asn | Gln | Glu | |
| | | | 180 | | | | | 185 | | | | | 190 | | | |
| cgt | ttg | gat | aac | ctg | cag | gct | gaa | ctc | ggc | cgg | ggc | aag | att | ctg | ccc | 624 |
| Arg | Leu | Asp | Asn | Leu | Gln | Ala | Glu | Leu | Gly | Arg | Gly | Lys | Ile | Leu | Pro | |
| | | 195 | | | | | 200 | | | | | 205 | | | | |
| ttg | gaa | gcc | gct | ctg | ccg | gaa | gct | gac | ttt | atc | gtg | tgg | gtc | gcc | agt | 672 |
| Leu | Glu | Ala | Ala | Leu | Pro | Glu | Ala | Asp | Phe | Ile | Val | Trp | Val | Ala | Ser | |
| 210 | | | | | 215 | | | | | 220 | | | | | | |
| atg | cct | cag | ggc | gta | gtg | atc | gac | cca | gca | acc | ctg | aag | caa | ccc | tgc | 720 |
| Met | Pro | Gln | Gly | Val | Val | Ile | Asp | Pro | Ala | Thr | Leu | Lys | Gln | Pro | Cys | |
| 225 | | | | | 230 | | | | | 235 | | | | | 240 | |
| gtc | cta | atc | gac | ggg | ggc | tac | ccc | aaa | aac | ttg | ggc | agc | aaa | gtc | caa | 768 |
| Val | Leu | Ile | Asp | Gly | Gly | Tyr | Pro | Lys | Asn | Leu | Gly | Ser | Lys | Val | Gln | |
| | | | | 245 | | | | | 250 | | | | | 255 | | |
| ggt | gag | ggc | atc | tat | gtc | ctc | aat | ggc | ggg | gta | gtt | gaa | cat | tgc | ttc | 816 |
| Gly | Glu | Gly | Ile | Tyr | Val | Leu | Asn | Gly | Gly | Val | Val | Glu | His | Cys | Phe | |

-continued

```
                260                 265                 270
gac atc gac tgg cag atc atg tcc gct gca gag atg gcg cgg ccc gag     864
Asp Ile Asp Trp Gln Ile Met Ser Ala Ala Glu Met Ala Arg Pro Glu
            275                 280                 285 cgc cag atg ttt gcc tgc ttt gcc gag gcg atg ctc ttg gaa ttt gaa     912
Arg Gln Met Phe Ala Cys Phe Ala Glu Ala Met Leu Leu Glu Phe Glu
        290                 295                 300 ggc tgg cat act aac ttc tcc tgg ggc cgc aac caa atc acg atc gag     960
Gly Trp His Thr Asn Phe Ser Trp Gly Arg Asn Gln Ile Thr Ile Glu
305                 310                 315                 320 aag atg gaa gcg atc ggt gag gca tcg gtg cgc cac ggc ttc caa ccc    1008
Lys Met Glu Ala Ile Gly Glu Ala Ser Val Arg His Gly Phe Gln Pro
                325                 330                 335 ttg gca ttg gca att tga                                            1026
Leu Ala Leu Ala Ile
                340
```

<210> SEQ ID NO 11
<211> LENGTH: 341
<212> TYPE: PRT
<213> ORGANISM: Synechococcus elongatus PCC7942

<400> SEQUENCE: 11

```
Met Phe Gly Leu Ile Gly His Leu Thr Ser Leu Glu Gln Ala Arg Asp
1               5                   10                  15

Val Ser Arg Arg Met Gly Tyr Asp Glu Tyr Ala Asp Gln Gly Leu Glu
            20                  25                  30

Phe Trp Ser Ser Ala Pro Pro Gln Ile Val Asp Glu Ile Thr Val Thr
        35                  40                  45

Ser Ala Thr Gly Lys Val Ile His Gly Arg Tyr Ile Glu Ser Cys Phe
    50                  55                  60

Leu Pro Glu Met Leu Ala Ala Arg Arg Phe Lys Thr Ala Thr Arg Lys
65                  70                  75                  80

Val Leu Asn Ala Met Ser His Ala Gln Lys His Gly Ile Asp Ile Ser
                85                  90                  95

Ala Leu Gly Gly Phe Thr Ser Ile Ile Phe Glu Asn Phe Asp Leu Ala
            100                 105                 110

Ser Leu Arg Gln Val Arg Asp Thr Thr Leu Glu Phe Glu Arg Phe Thr
        115                 120                 125

Thr Gly Asn Thr His Thr Ala Tyr Val Ile Cys Arg Gln Val Glu Ala
    130                 135                 140

Ala Ala Lys Thr Leu Gly Ile Asp Ile Thr Gln Ala Thr Val Ala Val
145                 150                 155                 160

Val Gly Ala Thr Gly Asp Ile Gly Ser Ala Val Cys Arg Trp Leu Asp
                165                 170                 175

Leu Lys Leu Gly Val Gly Asp Leu Ile Leu Thr Ala Arg Asn Gln Glu
            180                 185                 190

Arg Leu Asp Asn Leu Gln Ala Glu Leu Gly Arg Gly Lys Ile Leu Pro
        195                 200                 205

Leu Glu Ala Ala Leu Pro Glu Ala Asp Phe Ile Val Trp Val Ala Ser
    210                 215                 220

Met Pro Gln Gly Val Val Ile Asp Pro Ala Thr Leu Lys Gln Pro Cys
225                 230                 235                 240

Val Leu Ile Asp Gly Gly Tyr Pro Lys Asn Leu Gly Ser Lys Val Gln
                245                 250                 255

Gly Glu Gly Ile Tyr Val Leu Asn Gly Gly Val Val Glu His Cys Phe
```

```
                    260                 265                 270
Asp Ile Asp Trp Gln Ile Met Ser Ala Ala Glu Met Ala Arg Pro Glu
            275                 280                 285

Arg Gln Met Phe Ala Cys Phe Ala Glu Ala Met Leu Leu Glu Phe Glu
            290                 295                 300

Gly Trp His Thr Asn Phe Ser Trp Gly Arg Asn Gln Ile Thr Ile Glu
305                 310                 315                 320

Lys Met Glu Ala Ile Gly Glu Ala Ser Val Arg His Gly Phe Gln Pro
            325                 330                 335

Leu Ala Leu Ala Ile
            340

<210> SEQ ID NO 12
<211> LENGTH: 24
<212> TYPE: DNA
<213> ORGANISM: Artificial
<220> FEATURE:
<223> OTHER INFORMATION: Synthetic DNA

<400> SEQUENCE: 12
aaagaaaccg ctgctgcgaa attt                                      24

<210> SEQ ID NO 13
<211> LENGTH: 14
<212> TYPE: DNA
<213> ORGANISM: Artificial
<220> FEATURE:
<223> OTHER INFORMATION: Synthetic DNA

<400> SEQUENCE: 13
aaggagcgat cgcc                                                 14
```

ALDEHYDE SYNTHASE GENE, RECOMBINANT MICROORGANISM COMPRISING THE SAME, AND METHOD FOR PRODUCING ALKANE USING THE SAME

CROSS REFERENCE TO RELATED APPLICATIONS

The present application claims priority from Japanese patent application JP 2019-038198 filed on Mar. 4, 2019, the content of which is hereby incorporated by reference into this application.

BACKGROUND

Technical Field

The present disclosure relates to a novel aldehyde synthase gene having activity of converting an alcohol into an aldehyde, a recombinant microorganism comprising such gene, and a method for producing an alkane using the same.

In recent years, biofuels have drawn attention as energy sources that can alternate fossil fuels. Examples of biofuels that are currently used include bioethanols prepared from maize or sugarcane and biodiesel fuels mainly composed of fatty acid methyl ester prepared from vegetable oil. Such biofuels, however, suffer from problems such as oxidation deterioration, fluidity at low temperatures, or low spraying performance (Yoshimoto et al., 2009, J. Combust. Soc. Jpn., 51, 121-128; and Park et al., 2011, Fuel, 90, 633-639).

Meanwhile, next-generation biofuels that have overcome the problems of the biofuels mentioned above and are made of components more similar to those of fossil fuels have drawn attention. The next-generation biofuels utilize non-food-based biomass sources that are not used for foods. Extensive research has been made concerning next-generation biofuels, and medium-chain alkanes having 10 to 16 carbon atoms are said to be suitable for diesel or aviation fuels (Biotech. Adv., 30, 989-1000, 2012). An alkane is a main component of fossil fuels such as light oil or gasoline, and compared to bioethanol or biodiesel fuels has higher energy density or compatibility to current infrastructures.

A technique of coexpressing an acyl-ACP reductase (EC 1.2.1.80) and a decarbonylase (EC 4.1.99.5) in a cell to synthesize an alkane is known (U.S. Pat. No. 8,846,371). An acyl-ACP reductase converts acyl-ACP, which is a raw material for a fatty acid existing universally as a cytoplasm constituent of an organism, into an aldehyde. A decarbonylase converts an aldehyde into an alkane.

An acyl-ACP reductase is known to exhibit high substrate specificity for acyl-ACP having 18 carbon atoms and have a high ability of synthesizing an aldehyde having 18 carbon atoms (FEBS J, 280, 4773-4781, 2013). In contrast, it is known that substrate specificity of a decarbonylase is not high and a decarbonylase recognizes aldehydes with various chain lengths as substrates (PNAS, 110, 8, 3191-3196, 2013).

Several pathways for aldehyde synthesis are known: a pathway in which an aldehyde is synthesized from acyl-CoA with the aid of acyl-CoA reductase (EC 1.2.1.50); a pathway in which an aldehyde is synthesized from a fatty acid with the aid of carboxylic acid reductase (EC 1.2.99.6) or aldehyde dehydrogenase (EC 1.2.1.3); and a pathway in which an aldehyde is synthesized from an alcohol with the aid of alcohol dehydrogenase (EC 1.1.1.1) or alcohol oxidase (EC 1.1.3.13).

However, no effective methods for synthesizing medium-chain aldehydes having approximately 6 to 18 carbon atoms are known (Appl. Environ. Micro., 81, 6, 1892-1901, 2015). If such medium-chain aldehydes are synthesized, medium-chain alkanes can be synthesized with the use of a decarbonylase with low substrate specificity that recognizes aldehydes of various chain lengths as substrates.

When an aldehyde is to be synthesized in a microorganism, an aldehyde synthesized in a cell is reduced to an alcohol by an oxidoreductase, such as an endogenous alcohol dehydrogenase (Fatma et al., 2016, Metab. Eng., 37, 35-45). An alcohol dehydrogenase has high activity per protein. In general, an alcohol dehydrogenase reduces an aldehyde to an alcohol, but some alcohol dehydrogenases are known to oxidize an alcohol to an aldehyde (JP H07-313153 A (1995)).

SUMMARY

In the past, however, no enzymes having activity of synthesizing a medium-chain aldehyde that can be used for biofuels were known. Under the circumstances as described above, the present disclosure provides a novel aldehyde synthase gene having activity of synthesizing a medium-chain aldehyde, a recombinant microorganism comprising such gene, and a method for producing an alkane using the same.

To this end, we have conducted concentrated studies and discovered a novel aldehyde synthase comprising an amino acid sequence other than the amino acid sequence of the known aldehyde synthase and having activity of synthesizing a medium-chain aldehyde, thereby completing the present disclosure.

Specifically, the present disclosure includes the following.

(1) An aldehyde synthase gene encoding the protein (a) or (b) below:

(a) a protein comprising the amino acid sequence as shown in SEQ ID NO: 2; or (b) a protein comprising an amino acid sequence that has 70% or higher sequence identity to the amino acid sequence as shown in SEQ ID NO: 2 and conserves valine 36 and valine 322 and having activity of synthesizing an aldehyde from an alcohol.

(2) An aldehyde synthase encoded by the aldehyde synthase gene according to (1).

(3) An expression vector comprising the aldehyde synthase gene according to (1) and a regulatory region that regulates expression of such gene.

(4) A recombinant microorganism prepared by introducing the aldehyde synthase gene according to (1) into a host microorganism.

(5) The recombinant microorganism according to (4), wherein the host microorganism is a bacterium of *Escherichia coli* or *Klebsiella*.

(6) The recombinant microorganism according to (4), which further comprises the decarbonylase gene, the ferredoxin gene, and the ferredoxin reductase gene introduced thereinto.

(7) A method for producing an alkane comprising culturing the recombinant microorganism according to any of (4) to (6).

(8) The method for producing an alkane according to (7), wherein the recombinant microorganism is cultured in an alkaline medium.

(9) The method for producing an alkane according to (7), which further comprises recovering an alkane from a medium in which the recombinant microorganism is cultured.

(10) The method for producing an alkane according to (7), which further comprises recovering an alkane from a medium in which the recombinant microorganism is cultured and purifying the recovered alkane.

(11) The method for producing an alkane according to (7), which further comprises producing an alkane having 9 to 20 carbon atoms.

The aldehyde synthase gene according to the present disclosure encodes a protein comprising a novel amino acid sequence and having activity of synthesizing an aldehyde from an alcohol under alkaline conditions. With the use of the aldehyde synthase gene according to the present disclosure, accordingly, a recombinant microorganism with an improved alkane-synthesizing capacity can be obtained. In addition, alkane productivity in an alkane synthesis system involving the use of the recombinant microorganism comprising the aldehyde synthase gene according to the present disclosure introduced thereinto can be improved to a significant extent, and a remarkable cost reduction can be expected in alkane production.

DETAILED DESCRIPTION

Figure 1:
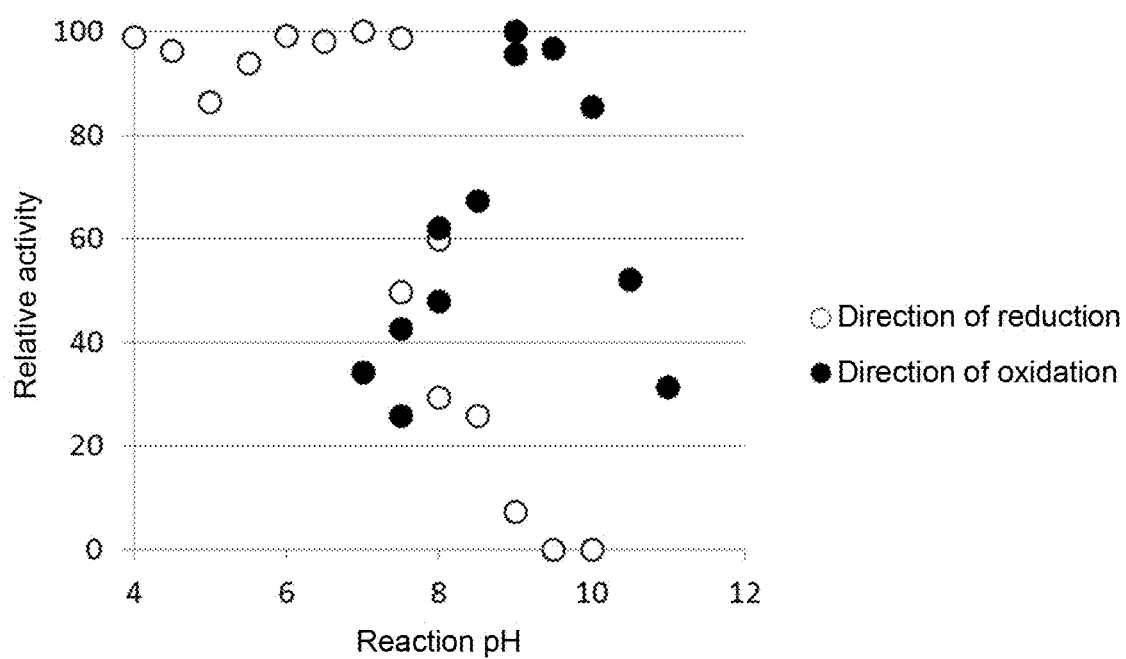
FIG. 1 shows a characteristic diagram demonstrating the results of measurement of enzymatic activity of the aldehyde synthase purified in Example 3 in terms of pH dependency.

Hereafter, the present disclosure is described in greater detail with reference to the figures and the examples.

<Aldehyde Synthase Gene>

The aldehyde synthase gene according to the present disclosure encodes a protein having activity of oxidizing an alcohol to synthesize an aldehyde. As described in the examples below, the aldehyde synthase gene according to the present disclosure encompasses a gene isolated from *Pantoea* sp. capable of high-level aldehyde production, which had been screened for with the use of, as indicators, the medium-chain alcohol oxidizing activity and the aldehyde synthesizing activity. As an alcohol dehydrogenase derived from *Pantoea* sp. AS-PWVM4, a 36.8 kDa protein encoded by the adhP gene has been known. The gene isolated from *Pantoea* sp. capable of high-level aldehyde production has been found to encode a novel protein in which 2 amino acid residues are different from those of the known alcohol dehydrogenase.

SEQ ID NO: 2 shows an amino acid sequence of a protein encoded by the gene isolated from *Pantoea* sp. capable of high-level aldehyde production, and SEQ ID NO: 1 shows a nucleotide sequence of a coding region of the gene. Such amino acid sequence differs from the amino acid sequence of an alcohol dehydrogenase encoded by the adhP gene derived from *Pantoea* sp. AS-PWVM4 in terms of valine in the 36th position and valine in the 322nd position from the N terminus of the amino acid sequence as shown in SEQ ID NO: 2. In the alcohol dehydrogenase encoded by the adhP gene derived from *Pantoea* sp. AS-PWVM4, an amino acid in the 36th position and an amino acid in the 322nd position from the N terminus are isoleucine and threonine, respectively.

The aldehyde synthase gene according to the present disclosure is not limited to a gene having a coding region comprising the nucleotide sequence as shown in SEQ ID NO: 1 or a gene encoding a protein comprising the amino acid sequence as shown in SEQ ID NO: 2. For example, a gene comprising an amino acid sequence having a high degree of similarity and/or identity to the amino acid sequence as shown in SEQ ID NO: 2 can be used, provided that valine 36 and valine 322 as described above are maintained. A specific example is a gene encoding a protein comprising an amino acid sequence exhibiting 50%, 60%, 70%, 80%, 85%, or 90% or higher identity to the amino acid sequence as shown in SEQ ID NO: 2 and having aldehyde synthesizing activity. Another specific example is a gene encoding a protein comprising an amino acid sequence exhibiting 80% or higher similarity, 85% or higher similarity, 90% or higher similarity, 95% or higher similarity, or 97% or higher similarity to the amino acid sequence as shown in SEQ ID NO: 2 and having aldehyde synthesizing activity.

The degree of sequence identity can be determined using the BLASTN or BLASTX Program equipped with the BLAST algorithm (at default settings). The degree of sequence identity is determined by subjecting a pair of amino acid sequences to pairwise alignment analysis, identifying completely identical amino acid residues, and calculating the percentage of the identified amino acid residues in all amino acid residues subjected to such comparison. The degree of sequence similarity is determined by subjecting a pair of amino acid sequences to pairwise alignment analysis, identifying completely identical amino acid residues and amino acid residues exhibiting similar functions, and calculating the percentage of the identified amino acid residues in all amino acid residues subjected to such comparison.

The aldehyde synthase gene according to the present disclosure is not limited to a gene encoding a protein comprising the amino acid sequence as shown in SEQ ID NO: 2. For example, it may be a protein comprising an amino acid sequence derived from the amino acid sequence as shown in SEQ ID NO: 2 by substitution, deletion, insertion, or addition of one or a plurality of amino acids, provided that valine 36 and valine 322 are maintained. In some embodiments, a plurality of amino acids may be several. For example, a plurality of amino acids may be 2 to 40, 2 to 30, 2 to 20, 2 to 10, or 2 to 5 amino acids.

Furthermore, the aldehyde synthase gene according to the present disclosure is not limited to a gene comprising a coding region comprising the nucleotide sequence as shown in SEQ ID NO: 1. For example, it may be a gene comprising a coding region comprising a polynucleotide hybridizing under stringent conditions to the full-length sequence or a partial sequence of a complementary strand of DNA comprising the nucleotide sequence as shown in SEQ ID NO: 1, provided that it encodes a protein maintaining valine 36 and valine 322. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, sodium concentration may be 25 to 500 mM, and temperature may be 42° C. to 68° C. In some other embodiments, sodium concentration may be 25 to 300 mM, and temperature may be 42° C. to 65° C. Further specifically, hybridization may be carried out in the presence of 5×SSC (83 mM NaCl, 83 mM sodium citrate) at 42° C.

In a protein comprising an amino acid sequence other than the amino acid sequence as shown in SEQ ID NO: 2 or a protein encoded by a nucleotide sequence other than the nucleotide sequence as shown in SEQ ID NO: 1, as described above, the positions of valine 36 and valine 322 may be different from the 36th and the 322nd positions mentioned above.

A method for preparing DNA comprising a nucleotide sequence encoding an aldehyde synthase comprising an amino acid sequence other than the amino acid sequence as shown in SEQ ID NO: 2 or DNA comprising a nucleotide sequence other than the nucleotide sequence as shown in SEQ ID NO: 1 is not particularly limited, and a known method can be adequately adopted. For example, given nucleotides can be substituted in accordance with a site-directed mutagenesis technique. Examples of site-directed mutagenesis techniques include a method of site-directed mutagenesis (i.e., the Kunkel method, Kunkel, T. A., Proc. Natl. Acad. Sci., U.S.A., 82, 488-492, 1985) and the Gapped duplex method. Alternatively, a mutation can be introduced with the use of, for example, a mutagenesis kit that adopts a site-directed mutagenesis technique (e.g., Mutan-K and Mutan-G, TAKARA SHUZO CO., LTD.) or an LA PCR in vitro Mutagenesis series kit (TAKARA SHUZO CO., LTD.).

A protein comprising an amino acid sequence other than the amino acid sequence as shown in SEQ ID NO: 2 or a protein encoded by DNA comprising a nucleotide sequence other than the nucleotide sequence as shown in SEQ ID NO: 1 has aldehyde synthesizing activity. This can be confirmed in accordance with a conventional technique. For example, an expression vector capable of expressing a gene encoding a target protein in a host (e.g., *E. coli*) is first constructed. Subsequently, a host is transformed with the aid of the constructed expression vector and the gene is expressed in the host. The host included in the culture solution is then disrupted via ultrasonic treatment, and unnecessary substances are then removed via centrifugation or other means to obtain a crude protein solution. Thereafter, the host is purified until a single band is observed via SDS-PAGE, and a purified protein encoded by such gene is then obtained. The resulting purified protein is used to confirm that the purified protein would oxidize a substrate alcohol (e.g., 1-tetradecanol) and generate an aldehyde (e.g., tetradecanal). When the substrate alcohol is decreased but an aldehyde generated, it can be concluded that a protein encoded by the gene has aldehyde synthase activity.

As described above, the novel aldehyde synthase gene of the present disclosure is capable of oxidizing a medium-chain alcohol and synthesizing a medium-chain aldehyde. A medium-chain aldehyde has 4 to 18 carbon atoms. In some other embodiments, a medium-chain aldehyde may have 6 to 14 or 6 to 12 carbon atoms. Such medium-chain aldehyde is used as a substrate for the decarbonylase as described below and converted into an alkane.

In particular, an aldehyde synthase encoded by the novel aldehyde synthase gene of the present disclosure catalyzes a reaction of oxidizing an alcohol to generate an aldehyde in the alkaline environment and it catalyzes an inverse reaction; i.e., a reaction of reducing an aldehyde to generate an alcohol, in an acidic environment. In a system of alcohol and/or aldehyde fermentation culture using a recombinant into which the novel aldehyde synthase gene of the present disclosure has been introduced, accordingly, the amount of an alcohol and/or an aldehyde synthesized can be regulated in a simple manner of modifying a pH level in the culture reaction. Since an alcohol and an aldehyde are intermediates of various metabolites, the novel aldehyde synthase gene of the present disclosure and a recombinant into which such aldehyde synthase gene have been introduced can be used for production of various substances.

<Decarbonylase Gene>

The decarbonylase gene encodes a protein having decarbonylase activity. The term "decarbonylase activity" refers to activity of decarbonylating an aldehyde compound (a substrate) to produce a hydrocarbon (alkane). As an example of a decarbonylase gene, SEQ ID NO: 5 shows the amino acid sequence of a wild-type decarbonylase encoded by the decarbonylase gene derived from *N. punctiforme* PCC 73102. SEQ ID NO: 4 shows the nucleotide sequence of the coding region of the decarbonylase gene derived from *N. punctiforme* PCC 73102.

The decarbonylase gene is not limited to the gene identified by SEQ ID NO: 4 and SEQ ID NO: 5. It may be a gene encoding a decarbonylase comprising an amino acid sequence other than the amino acid sequence as shown in SEQ ID NO: 5. An example of a decarbonylase comprising an amino acid sequence other than the amino acid sequence as shown in SEQ ID NO: 5 is a decarbonylase comprising an amino acid sequence having high similarity and/or identity to that of a decarbonylase encoded by the decarbonylase gene derived from the *N. punctiforme* PCC 73102 strain. A specific example thereof is a gene encoding a protein comprising an amino acid sequence exhibiting 50%, 60%, 70%, 80%, 85%, or 90% or higher identity to the amino acid sequence as shown in SEQ ID NO: 5 and having the decarbonylase activity as described above. Another specific example is a gene encoding a protein comprising an amino acid sequence exhibiting 80%, 85%, 90%, 95%, or 97% or higher similarity to the amino acid sequence as shown in SEQ ID NO: 5 and having the decarbonylase activity as described above.

The degree of sequence identity can be determined using the BLASTN or BLASTX Program equipped with the BLAST algorithm (at default settings). The degree of sequence identity is determined by subjecting a pair of amino acid sequences to pairwise alignment analysis, identifying completely identical amino acid residues, and calculating the percentage of the identified amino acid residues in all amino acid residues subjected to such comparison. The degree of sequence similarity is determined by subjecting a pair of amino acid sequences to pairwise alignment analysis, identifying completely identical amino acid residues and amino acid residues exhibiting similar functions, and calculating the percentage of the identified amino acid residues in all amino acid residues subjected to such comparison.

A decarbonylase comprising an amino acid sequence other than the amino acid sequence as shown in SEQ ID NO:

5 may be a protein comprising an amino acid sequence derived from the amino acid sequence as shown in SEQ ID NO: 5 by deletion, substitution, addition, or insertion of 1 to 50, 1 to 40, 1 to 30, or 1 to 20 amino acids and having decarbonylase activity.

Furthermore, a decarbonylase comprising an amino acid sequence other than the amino acid sequence as shown in SEQ ID NO: 5 may be a protein hybridizing under stringent conditions to the full-length sequence or a partial sequence of a complementary strand of DNA comprising the nucleotide sequence as shown in SEQ ID NO: 4 and having decarbonylase activity. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization.

A method for preparing DNA comprising a nucleotide sequence encoding a decarbonylase comprising an amino acid sequence other than the amino acid sequence as shown in SEQ ID NO: 5 or DNA comprising a nucleotide sequence other than the nucleotide sequence as shown SEQ ID NO: 4 is not particularly limited, and a known method can be adequately adopted. For example, given nucleotides can be substituted in accordance with a site-directed mutagenesis technique. Examples of site-directed mutagenesis techniques include a method of site-directed mutagenesis (i.e., the Kunkel method, Kunkel, T. A., Proc. Natl. Acad. Sci., U.S.A., 82, 488-492, 1985) and the Gapped duplex method. Alternatively, a mutation can be introduced with the use of, for example, a mutagenesis kit that adopts a site-directed mutagenesis technique (e.g., Mutan-K and Mutan-G, TAKARA SHUZO CO., LTD.) or an LA PCR in vitro Mutagenesis series kit (TAKARA SHUZO CO., LTD.).

A decarbonylase comprising an amino acid sequence exhibiting high degrees of similarity and/or identity to the decarbonylase encoded by the decarbonylase gene derived from *N. punctiforme* PCC 73102 can be identified with the use of databases storing protein amino acid sequence information (e.g., GenBank), and nucleotide sequence information and amino acid sequence information thereof can be obtained.

There are 4 other examples of decarbonylase genes: (1) decarbonylases typified by Npun_R1711 of *Nostoc punctiforme* (Science, Vol. 329, pp. 559-562, 2010); (2) a decarbonylase related to an aldehyde dehydrogenase (JP Patent No. 5,867,586); (3) long-chain alkane synthases typified by the Cer1 gene of *Arabidopsis thaliana* (Plant Cell, 24, 3106-3118, 2012); and (4) P450 alkane synthases typified by the CYP4G1 gene of *Drosophila melanogaster* (PNAS, 109, 37, 14858-14863, 2012).

More specific examples of (1) include Npun_R0380 of *Nostoc punctiforme* (a paralog of Npun_R1711), Nos7524_4304 of *Nostoc* sp., Anacy_3389 of *Anabaena cylindrica*, Aazo_3371 of *Anabaena azollae*, Cylst_0697 of *Cylindrospermum stagnale*, Glo7428_0150 of *Gloeocapsa* sp., Cal7507_5586 of *Calothrix* sp., FIS3754_06310 of *Fischerella* sp., Mic7113_4535 of *Microcoleus* sp., Chro_1554 of *Chroococcidiopsis hermalis*, GE17407_1564 of *Geitlerinema* sp., and Cyan8802_0468 of *Cyanothece* sp.

Specific examples of (2) include: BAE77705, BAA35791, BAA14869, BAA14992, BAA15032, BAA16524, BAE77705, BAA15538, and BAA15073 derived from *Escherichia coli* K-12 W3110; YP_001268218, YP_001265586, YP_001267408, YP_001267629, YP_001266090, YP_001270490, YP_001268439, YP_001267367, YP_001267724, YP_001269548, YP_001268395, YP_001265936, YP_001270470, YP_001266779, and YP_001270298 derived from *Pseudomonas* putida_F1; NP_388129, NP_389813, NP_390984, NP_388203, NP_388616, NP_391658, NP_391762, NP_391865, and NP_391675 derived from *Bacillus subtilis* 168; NP_599351, NP_599725, NP_601988, NP_599302, NP_601867, and NP_601908 derived from *Corynebacterium glutamicum* ATCC13032; YP_001270647 derived from *Lactobacillus reuteri* DSM20016; NP_010996, NP_011904, NP_015264, NP_013828, NP_009560, NP_015019, NP_013893, NP_013892, and NP_011902 derived from *Saccharomyces cerevisiae*; XP_002548035, XP_002545751, XP_002547036, XP_002547030, XP_002550712, XP_002547024, XP_002550173, XP_002546610, and XP_002550289 derived from *Candida tropicalis* MYA-3404; XP_460395, XP_457244, XP_457404, XP_457750, XP_461954, XP_462433, XP_461708, and XP_462528 derived from *Debaryomyces hansenii* CBS767; XP_002489360, XP_002493450, XP_002491418, XP_002493229, XP_002490175, XP_002491360, and XP_002491779 derived from *Pichia pastoris* GS115; NP_593172, NP_593499, and NP_594582 derived from *Schizosaccharomyces pombe*; XP_001822148, XP_001821214, XP_001826612, XP_001817160, XP_001817372, XP_001727192, XP_001826641, XP_001827501, XP_001825957, XP_001822309, XP_001727308, XP_001818713, XP_001819060, XP_001823047, XP_001817717, and XP_001821011 derived from *Aspergillus oryzae* RIB40; NP_001150417, NP_001105047, NP_001147173, NP_001169123, NP_001105781, NP_001157807, NP_001157804, NP_001105891, NP_001105046, NP_001105576, NP_001105589, NP_001168661, NP_001149126, and NP_001148092 derived from *Zea mays*; NP_564204, NP_001185399, NP_178062, NP_001189589, NP_566749, NP_190383, NP_187321, NP_190400, NP_001077676, and NP_175812 derived from *Arabidopsis thaliana*; NP_733183, NP_609285, NP_001014665, NP_649099, NP_001189159, NP_610285, and NP_610107 derived from *Drosophila melanogaster*; NP_001006999, XP_001067816, XP_001068348, XP_001068253, NP_113919, XP_001062926, NP_071609, NP_071852, NP_058968, NP_001011975, NP_115792, NP_001178017, NP_001178707, NP_446348, NP_071992, XP_001059375, XP_001061872, and NP_001128170 derived from *Rattus norvegicus*; NP_036322, NP_001193826, NP_001029345, NP_000684, NP_000680, NP_000683, NP_000681, NP_001071, NP_000687, NP_001180409, NP_001173, NP_000682, NP_000373, NP_001154976, NP_000685, and NP_000686 derived from *Homo sapiens*; and KPN_02991, KPN_1455, and KPN_4772 derived from *Klebsiella* sp. NBRC100048.

Specific examples of (3) include: AT1G02190 and AT1G02205 (CER1) of *Arabidopsis thaliana*: 4330012 of *Oryza sativa*; 101252060 of *Solanum lycopersicum*; CARUB_v10008547 mg of *Capsella rubella*; 106437024 of *Brassica napus*; 103843834 of *Brassica rapa*; EUTSA_v10009534 mg of *Eutrema salsugineum*; 104810724 of *Tarenaya hassleriana*; 105773703 of *Gossypium raimondii*; TCM_042351 of *Theobroma cacao*; 100243849 of *Vitis vinifera*; 105167221 of *Sesamum indicum*; 104442848 of

*Eucalyptus grandis;* 103929751 of *Pyrus bretschneideri;* 107618742 of *Arachis ipaensis;* and 103428452 of *Malus domestica.*

Specific examples of (4) include CYP4G1 of *Drosophila melanogaster,* 101887882 of *Musca domestica,* AaeL_ AAEL006824 of *Aedes aegypti,* and AgaP_AGAP000877 of *Anopheles gambiae.*

<Ferredoxin Gene>

When ferredoxin is allowed to be present in a system of synthesizing an alkane from an aldehyde with the aid of the decarbonylase, alkane productivity can be improved. When ferredoxin NADPH reductase is allowed to be present in addition to ferredoxin (this situation may be referred to as "ferredoxin NADP+reductase"), alkane productivity can further be improved to a significant extent.

A ferredoxin is an iron-sulfur protein comprising an iron-sulfur cluster (i.e., an Fe—S cluster) therein and it functions as an electron carrier. A ferredoxin gene is not particularly limited, and a gene derived from any organism species may be used. For example, nucleotide sequences of ferredoxin genes and amino acid sequences of ferredoxin derived from various organism species can be identified with reference to the databases storing gene information, such as DDBJ/EMBL/GenBank International Nucleotide Sequence Databases.

More specifically, the ferredoxin gene derived from the *Nostoc punctiforme* PCC73102 strain (YP_001865513) can be used as the ferredoxin gene, although the gene is not limited thereto. SEQ ID NO: 7 shows the amino acid sequence of the ferredoxin encoded by the ferredoxin gene derived from the *Nostoc punctiforme* PCC73102 strain. SEQ ID NO: 6 shows the nucleotide sequence of the coding region of the ferredoxin gene derived from the *Nostoc punctiforme* PCC73102 strain.

The ferredoxin gene is not limited to a gene encoding the amino acid sequence as shown in SEQ ID NO: 7. It may be a gene encoding a protein comprising an amino acid sequence having 70%, 80%, 90%, 95%, or 98% or higher identity to the amino acid sequence as shown in SEQ ID NO: 7 and functioning as ferredoxin. The degree of sequence identity can be determined using the BLASTN or BLASTX Program equipped with the BLAST algorithm (at default settings). The degree of sequence identity is determined by subjecting a pair of amino acid sequences to pairwise alignment analysis, identifying completely identical amino acid residues, and calculating the percentage of the identified amino acid residues in all amino acid residues subjected to such comparison.

The ferredoxin gene is not limited to a gene encoding the amino acid sequence as shown in SEQ ID NO: 7. It may be a gene encoding a protein comprising an amino acid sequence derived from the amino acid sequence as shown in SEQ ID NO: 7 by deletion, substitution, addition, or insertion of 1 to 20, 1 to 15, 1 to 10, or 1 to 5 amino acids and functioning as ferredoxin.

Furthermore, the ferredoxin gene is not limited to a gene comprising the nucleotide sequence as shown in SEQ ID NO: 6. For example, it may be a gene hybridizing under stringent conditions to the full-length sequence or a partial sequence of a complementary strand of DNA comprising the nucleotide sequence as shown in SEQ ID NO: 6 and encoding a protein that functions as ferredoxin. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization.

A method for preparing DNA comprising a nucleotide sequence encoding an amino acid sequence derived from the amino acid sequence as shown in SEQ ID NO: 7 by deletion, substitution, addition, or insertion of given amino acids or DNA comprising a nucleotide sequence other than the nucleotide sequence as shown in SEQ ID NO: 6 is not particularly limited, and a known method can be adequately adopted. For example, given nucleotides can be substituted in accordance with a site-directed mutagenesis technique. Examples of site-directed mutagenesis techniques include a method of site-directed mutagenesis (i.e., the Kunkel method, Kunkel, T. A., Proc. Natl. Acad. Sci., U.S.A., 82, 488-492, 1985) and the Gapped duplex method. Alternatively, a mutation can be introduced with the use of, for example, a mutagenesis kit that adopts a site-directed mutagenesis technique (e.g., Mutan-K and Mutan-G, TAKARA SHUZO CO., LTD.) or an LA PCR in vitro Mutagenesis series kit (TAKARA SHUZO CO., LTD.).

A ferredoxin NADPH reductase catalyzes the redox reactions between ferredoxin and NADPH. In order to allow both ferredoxin and ferredoxin NADPH reductase to be present in a system of synthesizing an alkane from an aldehyde with the aid of the decarbonylase, for example, a gene encoding ferredoxin and a gene encoding ferredoxin NADPH reductase may be introduced. A ferredoxin NADPH reductase gene is not particularly limited, and a gene derived from any organism species may be used. For example, nucleotide sequences of the ferredoxin NADPH reductase genes and amino acid sequences of the ferredoxin NADPH reductases derived from various organism species can be identified with reference to the databases storing gene information, such as DDBJ/EMBL/GenBank International Nucleotide Sequence Databases.

More specifically, the ferredoxin NADPH reductase gene derived from the *Nostoc punctiforme* PCC73102 strain (YP_001866231) can be used as the ferredoxin NADPH reductase gene, although the gene is not limited thereto. SEQ ID NO: 9 shows the amino acid sequence of the ferredoxin NADPH reductase encoded by the ferredoxin NADPH reductase gene derived from the *Nostoc punctiforme* PCC73102 strain. SEQ ID NO: 8 shows the nucleotide sequence of the coding region of the ferredoxin NADPH reductase gene derived from the *Nostoc punctiforme* PCC73102 strain.

The ferredoxin NADPH reductase gene is not limited to a gene encoding the amino acid sequence as shown in SEQ ID NO: 9. It may be a gene encoding a protein comprising an amino acid sequence exhibiting 70%, 80%, 90%, 95%, or 98% or higher identity to the amino acid sequence as shown in SEQ ID NO: 9 and functioning as a ferredoxin NADPH reductase. The degree of sequence identity can be determined using the BLASTN or BLASTX Program equipped with the BLAST algorithm (at default settings). The degree of sequence identity is determined by subjecting a pair of amino acid sequences to pairwise alignment analysis, identifying completely identical amino acid residues, and calculating the percentage of the identified amino acid residues in all amino acid residues subjected to such comparison.

The ferredoxin NADPH reductase gene is not limited to a gene encoding the amino acid sequence as shown in SEQ ID NO: 9. It may be a gene encoding a protein comprising an amino acid sequence derived from the amino acid sequence as shown in SEQ ID NO: 9 by deletion, substitution, addition, or insertion of 1 to 50, 1 to 40, 1 to 30, or 1 to 20 amino acids and functioning as a ferredoxin NADPH reductase.

Furthermore, the ferredoxin NADPH reductase gene is not limited to a gene comprising the nucleotide sequence as shown in SEQ ID NO: 8. For example, it may be a gene hybridizing under stringent conditions to the full-length sequence or a partial sequence of a complementary strand of DNA comprising the nucleotide sequence as shown in SEQ ID NO: 8 and encoding a protein that functions as a ferredoxin NADPH reductase. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization.

A method for preparing DNA comprising a nucleotide sequence encoding an amino acid sequence derived from the amino acid sequence as shown in SEQ ID NO: 9 by deletion, substitution, addition, or insertion of given amino acids or DNA comprising a nucleotide sequence other than the nucleotide sequence as shown in SEQ ID NO: 9 is not particularly limited, and a known method can be adequately adopted. For example, given nucleotides can be substituted in accordance with a site-directed mutagenesis technique. Examples of site-directed mutagenesis techniques include a method of site-directed mutagenesis (i.e., the Kunkel method, Kunkel, T. A., Proc. Natl. Acad. Sci., U.S.A., 82, 488-492, 1985) and the Gapped duplex method. Alternatively, a mutation can be introduced with the use of, for example, a mutagenesis kit that adopts a site-directed mutagenesis technique (e.g., Mutan-K and Mutan-G, TAKARA SHUZO CO., LTD.) or an LA PCR in vitro Mutagenesis series kit (TAKARA SHUZO CO., LTD.).

<Acyl-ACP Reductase Gene>

An aldehyde utilized by the decarbonylase as a substrate is not limited to an aldehyde synthesized from an alcohol by an aldehyde synthase encoded by the aldehyde synthase gene according to the present disclosure. For example, an aldehyde may be synthesized from an acyl-ACP reductase gene that catalyzes conversion of acyl-ACP into fatty aldehyde. In other words, the acyl-ACP reductase gene may be used to provide an aldehyde that serves as a substrate for the decarbonylase.

The acyl-ACP reductase gene is not particularly limited, and any gene encoding the acyl-ACP reductase registered as EC 1.2.1.80 can be used. Examples of acyl-ACP reductase genes include Synpcc7942_1594 of *Synechococcus elongatus*, M744_09025 of *Synechococcus* sp., LEP3755_23580 of *Leptolyngbya* sp., Glo7428_0151 of *Gloeocapsa* sp., Nos7107_1027 of *Nostoc* sp., Ava_2534 of *Anabaena variabilis*, IJ00_07395 of *Calothrix* sp., Cri9333_4415 of *Crinalium epipsammum*, and FIS3754_06320 of *Fischerella* sp.

For example, the acyl-ACP reductase gene derived from *Synechococcus elongatus* PCC 7942 encodes a protein comprising the amino acid sequence as shown in SEQ ID NO: 11. The acyl-ACP reductase gene may encode a protein comprising an amino acid sequence having 60%, 70%, 80%, 90%, 95%, or 98% or higher identity to the amino acid sequence as shown in SEQ ID NO: 11 and having acyl-ACP reductase activity.

The degree of sequence identity can be determined using the BLASTN or BLASTX Program equipped with the BLAST algorithm (at default settings). The degree of sequence identity is determined by subjecting a pair of amino acid sequences to pairwise alignment analysis, identifying completely identical amino acid residues, and calculating the percentage of the identified amino acid residues in all amino acid residues subjected to such comparison.

The acyl-ACP reductase gene is not limited to a gene encoding the amino acid sequence as shown in SEQ ID NO: 11. It may be a gene encoding a protein comprising an amino acid sequence derived from the amino acid sequence as shown in SEQ ID NO: 11 by deletion, substitution, addition, or insertion of 1 to 50, 1 to 40, 1 to 30, or 1 to 20 amino acids and functioning as an acyl-ACP reductase.

Furthermore, the acyl-ACP reductase gene is not limited to a gene comprising the nucleotide sequence as shown in SEQ ID NO: 10. For example, it may be a gene hybridizing under stringent conditions to the full-length sequence or a partial sequence of a complementary strand of DNA comprising the nucleotide sequence as shown in SEQ ID NO: 10 and encoding a protein that functions as an acyl-ACP reductase. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization.

A method for preparing DNA comprising a nucleotide sequence encoding an amino acid sequence derived from the amino acid sequence as shown in SEQ ID NO: 11 by deletion, substitution, addition, or insertion of given amino acids or DNA comprising a nucleotide sequence other than the nucleotide sequence as shown in SEQ ID NO: 10 is not particularly limited, and a known method can be adequately adopted. For example, given nucleotides can be substituted by a site-directed mutagenesis technique. Examples of site-directed mutagenesis techniques include a method of site-directed mutagenesis (i.e., the Kunkel method, Kunkel, T. A., Proc. Natl. Acad. Sci., U.S.A., 82, 488-492, 1985) and the Gapped duplex method. Alternatively, a mutation can be introduced with the use of, for example, a mutagenesis kit that adopts a site-directed mutagenesis technique (e.g., Mutan-K and Mutan-G, TAKARA SHUZO CO., LTD.) or an LA PCR in vitro Mutagenesis series kit (TAKARA SHUZO CO., LTD.).

In place of the acyl-ACP reductase gene, a gene encoding an enzyme that synthesizes an aldehyde serving as a substrate for the decarbonylase mutant can be used.

For example, a gene encoding a long chain fatty acyl-CoA reductase (EC.1.2.1.50), such as plu2079 (luxC) of *Photorhabdus luminescens*, PAU_02514 (luxC) of *Photorhabdus asymbiotica*, VF_A0923 (luxC) of *Aliivibrio fischeri*, VIBHAR_06244 of *Vibrio campbellii*, or Swoo_3633 of *Shewanella woodyi*, can be used. Also, genes encoding acyl-CoA reductases described in JP 2015-226477 A, such as 100776505 and 100801815 of *Glycine max*, can be used. In addition, any gene encoding an enzyme that can synthesize an aldehyde can be used without particular limitation. For example, genes encoding enzymes, such as alcohol dehydrogenase (EC.1.1.1.1), alcohol oxidase (EC. 1.1.3.13), aldehyde dehydrogenase (EC. 1.2.1.3), and carboxylate reductase (EC. 1.2.99.6), can be used.

<Recombinant Microorganisms>

The aldehyde synthase gene according to the present disclosure and the decarbonylase gene are introduced into a host microorganism, so that a recombinant microorganism capable of synthesizing an alkane can be prepared. A microorganism into which the aldehyde synthase gene according to the present disclosure is to be introduced is not particularly limited. Examples thereof include bacteria of *Escherichia coli* and *Klebsiella*. Yeast strains may be used as microorganisms into which the aldehyde synthase gene and the decarbonylase gene according to the present disclosure are to be introduced. While yeast strains are not particularly limited, examples thereof include a yeast strain that belongs to the genus *Pichia* such as *Pichia stipitis*, a yeast strain that belongs to the genus *Saccharomyces* such as *Saccharomyces cerevisiae*, and yeast strains that belong to the genus *Candida* such as *Candida tropicalis* and *Candida prapsilosis*.

When the aldehyde synthase gene, the decarbonylase gene, the ferredoxin gene, the ferredoxin NADPH reductase gene, and the acyl-ACP reductase gene are introduced into hosts, for example, a DNA fragment containing such genes may be inserted into an expression vector that can function in a host microorganism (e.g., a multiple-copy vector) to prepare recombinant DNA, and the resulting recombinant DNA may then be introduced into a microorganism to transform the microorganism. Expression vectors that can be used are not particularly limited, and a plasmid vector or a chromosome transfer vector that can be integrated into the genome of the host organism can be used. An expression vector is not particularly limited, and an available expression vector may be adequately selected in accordance with a host microorganism. Examples of expression vectors include plasmid DNA, bacteriophage DNA, retrotransposon DNA, and yeast artificial chromosome (YAC) DNA.

Examples of plasmid DNA include: YCp-type *E. coli*-yeast shuttle vectors, such as pRS413, pRS414, pRS415, pRS416, YCp50, pAUR112, and pAUR123; YEp-type *E. coli*-yeast shuttle vectors, such as pYES2 and YEp13; YIp-type *E. coli*-yeast shuttle vectors, such as pRS403, pRS404, pRS405, pRS406, pAUR101, and pAUR135; *E. coli*-derived plasmids (e.g., ColE plasmids, such as pBR322, pBR325, pUC18, pUC19, pUC118, pUC119, pTV118N, pTV119N, pBluescript, pHSG298, pHSG396, and pTrc99A, p15A plasmids, such as pACYC177 and pACYC184, and pSC101 plasmids, such as pMW118, pMW119, pMW218, and pMW219); *Agrobacterium*-derived plasmids (e.g., pBI101); and *Bacillus subtilis*-derived plasmids (e.g., pUB110 and pTP5). Examples of phage DNA include λ phage (e.g., Charon4A, Charon21 A, EMBL3, EMBL4, λgt10, λgt11, and λZAP), φX174, M13mp18, and M13mp19. An example of retrotransposon is a Ty factor. An example of a YAC vector is pYACC2. In addition, animal virus vectors, such as retrovirus or vaccinia virus vectors, and insect virus vectors, such as baculovirus vectors, can be used.

It is necessary that the genes mentioned above be integrated into an expression vector in an expressible state. In an expressible state, the genes are linked to promoters, and the resultants are integrated into a vector in that state, so that the genes are expressed under the control of given promoters in a host organism. In addition to the genes mentioned above, a promoter, a terminator, a cis element such as an enhancer according to need, a splicing signal, a poly A addition signal, a selection marker, a ribosome binding sequence (SD sequence), and the like can be linked to the expression vector. Examples of selection markers include antibiotic resistant genes, such as ampicillin resistant gene, kanamycin resistant gene, and hygromycin resistant gene.

As a method of transformation involving the use of an expression vector, a conventional technique can be adequately employed. Examples of methods of transformation include the calcium chloride method, the competent cell method, the protoplast or spheroplast method, and the electropulse method.

Alternatively, the genes may be introduced to increase the number of copies thereof. Specifically, the genes may be introduced in a manner such that multiple copies thereof would be present in chromosome DNA of the microorganism. Multiple copies of the genes can be introduced into chromosome DNA of the microorganism via homologous recombination with the use of multiple copies of target sequences that are present in chromosome DNA.

The gene expression level can be elevated by, for example, a method in which an expression regulatory sequence such as a promoter of the introduced gene is substituted with a sequence that can express the gene of interest at a higher level or a method in which a regulator to elevate the expression level of a given gene is introduced. Examples of promoters that enable high-level gene expression include, but are not particularly limited to, lac promoter, trp promoter, trc promoter, and pL promoter.

<Alkane Production>

As described above, an alkane can be synthesized with improved productivity with the use of a recombinant microorganism into which the aldehyde synthase gene and the decarbonylase gene according to the present disclosure have been introduced. Also, a recombinant microorganism into which the ferredoxin gene, the ferredoxin NADPH reductase gene, and the acyl-ACP reductase gene have been introduced in addition to the genes mentioned above may be used, so that an alkane can be synthesized with higher productivity. In a system involving the use of such recombinant microorganisms, culture can be conducted in a medium suitable for such microorganisms, and an alkane can be produced in the medium. According to the present disclosure, more specifically, the alkane-synthesizing capacity with the aid of an alkane synthase can be improved, and alkane productivity can be improved as a consequence.

According to the present disclosure, an alkane to be produced may have, for example, 9 to 20, 14 to 17, or 13 to 16 carbon atoms, although the number of carbon atoms is not limited thereto. An alkane is a solution with high viscosity, and it can be used for light oil (diesel oil) or aircraft fuel. Such alkane can be isolated from a reaction system in which the recombinant microorganisms were cultured in accordance with a conventional technique and then purified. By adopting the method described in Engineering in Life Sciences, vol. 16: 1, pp. 53-59, "Biosynthesis of chain-specific alkanes by metabolic engineering in *Escherichia coli*," a short-chain alkane can be synthesized.

In particular, an aldehyde synthase encoded by the aldehyde synthase gene according to the present disclosure exhibits higher aldehyde-synthesizing activity in an alkaline environment. When culturing the recombinant microorganisms mentioned above, accordingly, a pH level of the medium is adjusted to be higher than 7.0. In some embodiments, a pH level may be 7.1 to 8.5, or it may be 7.1 to 7.5. Thus, alkane productivity can further be improved.

EXAMPLES

Hereafter, the present disclosure is described in greater detail with reference to the examples, although the technical scope of the present disclosure is not limited to the following examples.

In the examples below, a microorganism capable of synthesizing an aldehyde with the use of an alcohol was identified, the aldehyde synthase gene was isolated from the identified microorganism, and a recombinant microorganism and an alkane synthesis system utilizing the isolated aldehyde synthase gene were constructed. All the reagents were purchased from Wako Pure Chemicals, unless otherwise specified.

Example 1

Approximately 850 strains were isolated from soil etc. Subsequently, approximately a small spatulaful of strains was added to 1 ml of 100 mM potassium phosphate buffer (pH 7.0) containing 1 mM 1-tetradecanol (Tokyo Chemical Industry Co., Ltd.), 3 mM NAD$^+$ (Oriental Yeast Co., Ltd.), 3 mM NADP$^+$ (Oriental Yeast Co., Ltd.), and a 0.5% (v/v) TritonX-100 solution, and the reaction was allowed to proceed at 28° C. and 300 rpm for 4 hours. Thereafter, the reaction product was centrifuged at 3,000 rpm for 10 minutes, 100 µl of the supernatant was collected, and the collected supernatant was then subjected to absorbance analysis. The supernatant (100 µl) of the reaction solution was fractionated to a 96-well microplate, and the absorbance at 340 nm was measured using a microplate reader (Spectra Max Plus384, Molecular devices CA, U.S.A.). A reaction solution to which no strains were added was designated as a blank sample, and the absorbance was corrected. The strains exhibiting the absorbance increased by approximately 0.1 times compared with the control sample without substrate were subjected to secondary screening.

Example 2

The strains selected as a result of primary screening via absorbance analysis in Example 1 were subjected to secondary screening. At the outset, approximately a small spatulaful of air-dried strains was added to 1 ml of 100 mM potassium phosphate buffer (pH 7.0) containing 2 mM 1-tetradecanol (Tokyo Chemical Industry Co., Ltd.), 5 mM NAD$^+$ (Oriental Yeast Co., Ltd.), 5 mM NADP$^+$ (Oriental Yeast Co., Ltd.), and a 0.5% (v/v) TritonX-100 solution, and the reaction was allowed to proceed at 28° C. and 300 rpm for 24 hours. Thereafter, 200 µl of 1 N HCl, 500 µl of saturated saline, and 100 µl of the internal standard (a solution of 5 mM 1-octadecanol in methanol) were added to the reaction solution, the mixture was subjected to extraction with 1 ml of toluene, and the resultant was subjected to gas chromatography analysis (Shimadzu Corporation). Analytical conditions were determined as described below.
Column: Nukol, 30 m×0.25 mm I.D. column (SUPELCO)
Detector (temperature): FID (200° C.)
Injection method: split
Carrier gas (pressure): He (100 kPa/cm$^2$)
Temperature of vaporizing chamber: 200° C.
Duration of analysis: 60 minutes
Temperature gradient: 80° C. (the initial temperature) to 112.5° C. at 5° C./min, to 190° C. at 40° C./min, and kept at 190° C. for 51.56 min As a result, generation of tetradecanal was observed in 21 strains in total, and generation of tetradecanoic acid was observed in 46 strains (generation of both tetradecanal and tetradecanoic acid was observed in 18 strains among the strains mentioned above). *Pantoea* sp. was selected from among these strains as a strain exhibiting high 1-tetradecanol oxidizing activity.

Example 3

In Example 3, the aldehyde synthase gene was identified from *Pantoea* sp. that had been identified as a microorganism having improved aldehyde synthesizing capacity. At the outset, *Pantoea* sp. identified in Example 2 was cultured in a medium comprising 0.5% (NH$_4$)$_2$SO$_4$, 0.1% NH$_4$Cl, 0.1% KH$_2$PO$_4$, 0.3% K$_2$HPO$_4$, 0.05% MgSO$_4$, 0.001% FeSO$_4$, 0.1% yeast extract, 1% tetradecanol, and 0.1% TritonX-100 at 28° C. and 300 rpm for 24 hours.

After the completion of culture, the cultured cells were recovered via centrifugation and then subjected to ultrasonic disruption. Thereafter, the resultant was centrifuged at 5,000 g and 4° C. for 15 minutes, and the supernatant was recovered. The recovered supernatant was further subjected to ultracentrifugation at 100,000 g, 4° C. for 1 hour to remove unnecessary matter. The soluble fraction thus obtained was subjected to ammonium sulfate precipitation, applied to HiTrap phenyl HP, Superdex 200 increase 10/300 GL, Hi Trap Q sepharose XL columns, and purified to achieve substantially a single band via SDS PAGE.

Enzymatic activity was measured in the manner described below. At the outset, 1 ml of 100 mM Tris (HCl) buffer (pH 8.5) containing 3 mM NAD$^+$ (Oriental Yeast Co., Ltd.), 3 mM NADP$^+$ (Oriental Yeast Co., Ltd.), a 0.01% (v/v) TritonX-100 solution, and 10 µl of an enzyme solution was allowed to stand at room temperature for 3 minutes, 1-tetradecanol (final concentration: 1 mM; Tokyo Chemical Industry Co., Ltd.) was added thereto to initiate the reaction, and the absorbance at 340 nm was measured. A unit was designated as the amount of an enzyme that converts 1 µmol of the substrate per minute (µmol/min). The reaction was allowed to proceed at 25° C.

The purified protein having aldehyde synthase activity was subjected to N-terminal amino acid sequence analysis, and the sequence MNMKIKTTMKAAVVKSFGEP (SEQ ID NO: 3) was obtained. The sequence of the aldehyde synthase gene was determined based on the sequence mentioned above. As a result, the sequence of interest was found to be the same as the sequence of the alcohol dehydrogenase of the adhP gene (36.8 kDa) of *Pantoea* sp. AS-PWVM4 except for amino acids at two sites. SEQ ID NO: 1 shows the nucleotide sequence of the coding region of the aldehyde synthase gene derived from *Pantoea* sp. having improved aldehyde synthesis capacity identified in this example, and SEQ ID NO: 2 shows the amino acid sequence of the protein encoded by the aldehyde synthase gene. In the sequence of the adhP gene of *Pantoea* sp. AS-PWVM4, amino acids corresponding to valine in the 36th position and valine in the 322nd position from the N terminus of the sequence as shown in SEQ ID NO: 2 were isoleucine and threonine, respectively.

Example 4

In Example 4, activity of the aldehyde synthase encoded by the aldehyde synthase gene isolated in Example 3 was examined in terms of pH dependency.

At the outset, the genes cloned in Example 3 were integrated in-frame into the SalI site and the NotI site of the pET21b(+) vector to construct an expression vector, pET21b (+)-adhP. *E. coli* Rosetta2 was transformed using the vector, and the cloned genes were expressed via IPTG induction. The culture solution was subjected to ultrasonic disruption and then ultracentrifugation at 100,000 g and 4° C. for 1 hour to remove unnecessary matter. The resulting crude enzyme was further purified with Superdex 200 increase 10/300 GL until a single band was detected via SDS PAGE. The pH profiles were measured using the crude enzyme.

In Example 4, enzyme activity was measured in the same manner as in Example 3. Specifically, 1 ml of a buffer containing 3 mM NAD$^+$ (Oriental Yeast Co., Ltd.), 3 mM NADP$^+$ (Oriental Yeast Co., Ltd.), a 0.01% (v/v) TritonX-100 solution, and 10 µl of an enzyme solution was allowed to stand at room temperature for 3 minutes, 1-tetradecanol (final concentration: 1 mM; Tokyo Chemical Industry Co., Ltd.) was added thereto to initiate the reaction, and the absorbance at 340 nm was measured. A unit was designated as the amount of an enzyme that converts 1 µmol of the substrate per minute (µmol/min). The reaction was allowed to proceed at 25° C. In this reaction, a 100 mM acetate buffer was used when the pH level of the reaction solution was adjusted to 5.0 or 5.5, a 100 mM potassium phosphate buffer was used when the pH level of the reaction solution was adjusted to 6.0, 6.5, 7.0, 7.5, or 8.0, a 100 mM Tris (HCl) buffer was used when the pH level of the reaction solution was adjusted to 7.5, 8.0, 8.5, or 9.0, and a 100 mM NaHCO$_3$/Na$_2$CO$_3$ buffer was used when the pH level of the reaction solution was adjusted to 9.0, 9.5, or 10.0.

FIG. 1 shows relative activity by designating the activity attained with the use of a 100 mM Tris (HCl) buffer (pH 8.5) to be 100. In FIG. 1, a dot line indicates relative activity of a reaction of reducing an aldehyde to an alcohol, and a solid line indicates relative activity of a reaction of oxidizing an alcohol to an aldehyde. As shown in FIG. 1, the purified aldehyde synthase catalyzed the reaction of reducing an aldehyde to an alcohol on an acidic side from pH 7.0-8.0 of the reaction solution, and it catalyzed the reaction of oxidizing an alcohol to an aldehyde on an alkaline side from pH 7.0-8.0.

Example 5

In Example 5, substrate specificity of the aldehyde synthase purified in Example 4 was examined.

Figure 2:
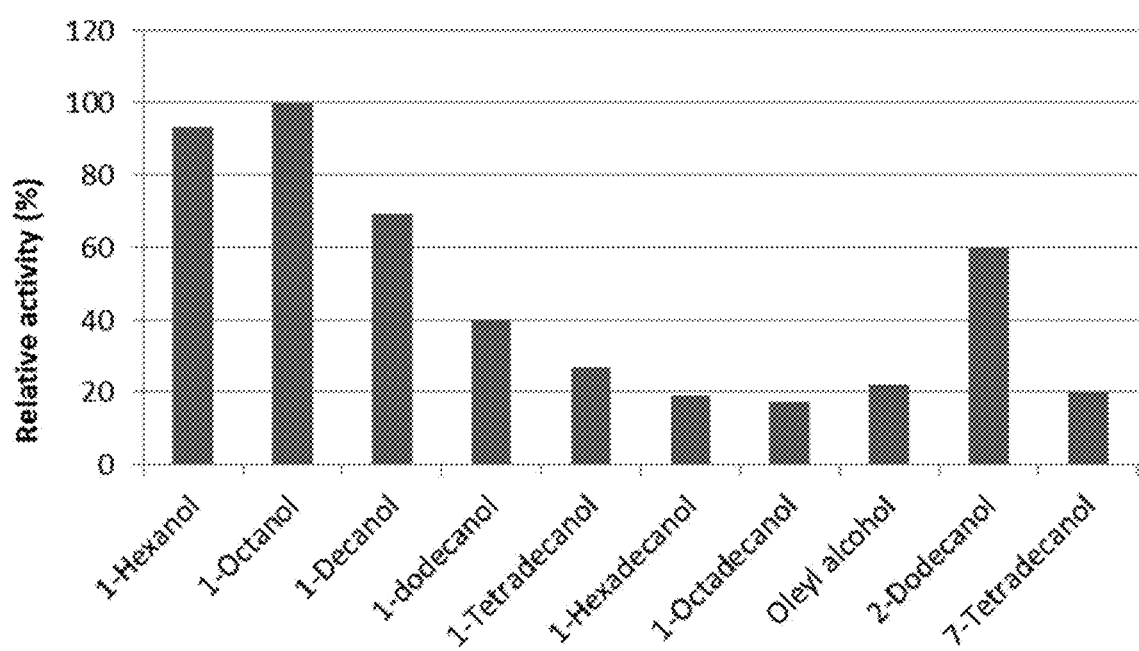
FIG. 2 shows a characteristic diagram demonstrating the results of examining substrate specificity of the aldehyde synthase purified in Example 3.

In Example 5, enzymatic activity was measured in the same manner as in Example 3, except that 1-tetradecanol contained as the substrate in the reaction solution was replaced with another alcohol. The results are shown in FIG. 2. In FIG. 2, the vertical axis indicates the relative value based on the activity of I-octanol exhibiting the highest reactivity designated to be 100. As shown in FIG. 2, it was found in the example that the aldehyde synthase purified in Example 4 was reactive with 1-hexanol having 6 carbon atoms to 7-tetradenol having 14 carbon atoms. The aldehyde synthase purified in Example 4 was also found to exhibit high substrate specificity to medium-chain alcohols having 6 to 10 carbon atoms including 1-octanol. In addition, the aldehyde synthase purified in Example 4 was found to be reactive with a secondary alcohol.

Example 6

In Example 6, a recombinant organism expressing the aldehyde synthase gene obtained in Example 3 was prepared.

At the outset, the aldehyde synthase gene obtained in Example 3 was inserted into a site between the SalI site and the NotI site of MCS1 of pRSF-Duet (Novagen) (a His-tag sequence is added to the N terminus upon expression), and the sequence of the decarbonylase gene (Nostoc *punctiforme* PCC73102, YP_001865325) was inserted into a site between the NdeI site and the XhoI site of MCS2. SEQ ID NO: 4 and SEQ ID NO: 5 each show the nucleotide sequence of the decarbonylase gene derived from *Nostoc punctiforme* PCC73102 and the amino acid sequence of the protein encoded by such gene. ATG included in the nucleotide sequence of the NdeI site is added to the decarbonylase gene inserted into MCS2. Upon gene expression, accordingly, an enzyme is synthesized to comprise an excessive methionine residue at the N terminus. Also, the obtained expression vector was designated as pRSF-Duet-adhP-NpAD.

The DNA sequence of the ferredoxin gene (*Nostoc punctiforme* PCC73102, YP_001865513) and that of the ferredoxin NADP reductase gene (*Nostoc punctiforme* PCC73102, YP_001866231) with the codons optimized for *E. coli* were synthesized. When synthesizing the DNA sequences of such genes, the GAA sequence was inserted after the initiation codon and the second amino acid from the N terminus was adjusted to be glutamic acid, so as to stabilize the protein. SEQ ID NO: 6 and SEQ ID NO: 7 each show the nucleotide sequence of the ferredoxin gene designed in this example and the amino acid sequence of the protein encoded by such gene. SEQ ID NO: 8 and SEQ ID NO: 9 each show the nucleotide sequence of the ferredoxin NADP reductase gene designed in this example and the amino acid sequence of the protein encoded by such gene.

The synthetic DNA sequences were inserted into a site between the NcoI site and the NotI site of pCDF-Duet (Novagen) and a site between the NdeI site and the XhoI site of pCDF-Duet. The obtained vector was designated as pCDF-Duet-fd-fdr.

Subsequently, *E. coli* Rosetta2 (DE3) (Novagen) was transformed using these 2 vectors. The obtained transformant was designated as *E. coli* Rosetta2 (DE3)/pRSF-Duet-adhP-NpAD/pCDF-Duet-fd-fdr.

Subsequently, the transformants were cultured, and the strains were recovered via centrifugation. To 1 ml of 100 mM potassium phosphate buffer (pH 7.5) containing 2.5 mM 1-tetradecanol (Tokyo Chemical Industry Co., Ltd.), 5 mM NAD$^+$ (Oriental Yeast Co., Ltd.), 5 mM NADPH (Oriental Yeast Co., Ltd.), and a 0.1% (v/v) TritonX-100 solution, 20 mg to 60 mg of the recovered strains were added, and the resultant was cultured with shaking at 30° C. and 120 rpm for 20 hours. After the completion of the reaction, gas chromatography analysis was carried out in accordance with Example 2, and the substrate and the product (1-dodecanol, myristic acid, 1-tetradecanal, and tridecane) were quantified.

Figure 3:
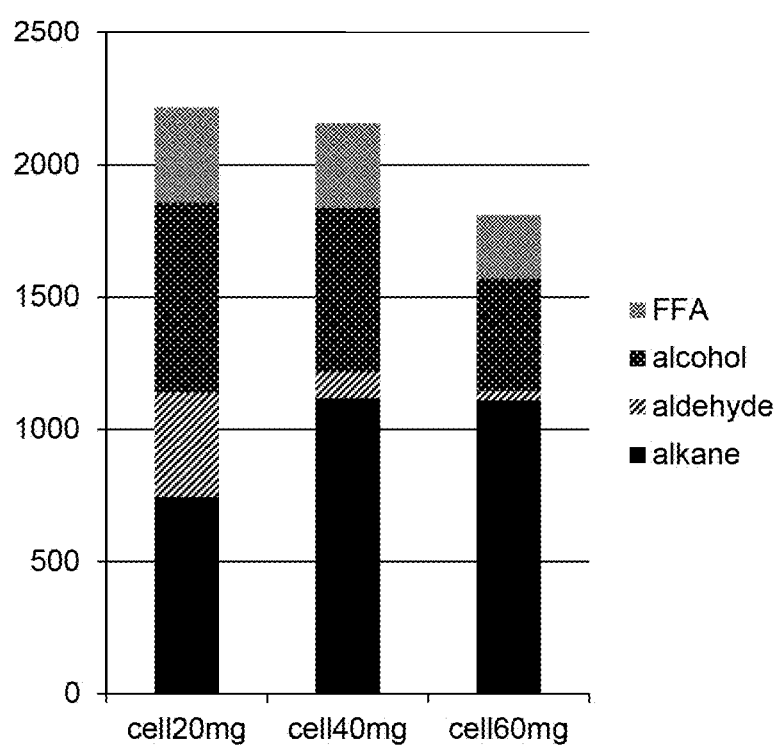
FIG. 3 shows a characteristic diagram demonstrating the results of alkane synthesis performed with the use of the transformant into which the aldehyde synthase gene isolated in Example 3 has been introduced.

The results are shown in FIG. 3. As shown in FIG. 3, the maximal amount of alkane production was achieved when 40 mg of the strains were used. In such a case, 1.11 mM alkane (tridecane) could be synthesized from 2.5 mM alcohol (1-tetradecanol), and the conversion yield reached 44.7%.

Example 7

In Example 7, effects of the aldehyde synthase gene obtained in Example 3 for improving alkane productivity were examined using the strains into which the acyl-ACP reductase gene had been introduced.

At the outset, the DNA sequence of the long-chain acyl-ACP reductase gene (*Synechococcus elongatus* PCC7942, YP_40061) was inserted into a site downstream of the NpAD gene in pRSF-Duet-adhP-NpAD prepared in Example 6 by the SLiCE method (Z Seamless Ligation Cloning Extract). In this case, a sequence was designed to comprise the DNA sequence of the long-chain acyl-ACP reductase gene inserted downstream of the S-tag sequence located downstream of MCS2: AAAGAAACCGCTGCTGCGAAATTT (SEQ ID NO: 12) via an artificial sequence: AAGGAGCGATCGCC (SEQ ID NO: 13). This artificial sequence comprises an rbs sequence, and polycistronic expression of the gene is realized. SEQ ID NO: 10 and SEQ ID NO: 11 each show the nucleotide sequence of the long-chain acyl-ACP reductase gene derived from *Synechococcus elongatus* PCC7942 and the amino acid sequence of the protein encoded by such gene. The resulting vector was designated as pRSF-Duet-adhP-NpAD-SeAR.

Subsequently, the DNA sequences of the decarbonylase gene (*Nostoc punctiforme* PCC73102, YP_001865325; SEQ ID NO: 4 and SEQ ID NO: 5) and the DNA sequence of the long-chain acyl-ACP reductase gene (*Synechococcus elongatus* PCC7942, YP_400611; SEQ ID NO: 10 and SEQ ID NO: 11) were integrated in-frame into a site between the PstI site and the NdeI site of pRSF-Duet (Novagen). The resulting vector was designated as pRSF-Duet-NpAD-SeAR. NpAD is synthesized in a manner such that the His-tag sequence derived from pRSF-Duet is added to the N terminus.

Subsequently, *E. coli* Rosetta2 (DE3) (Novagen) was transformed using pRSF-Duet-adhP-NpAD-SeAR and pCDF-Duet-fd-fdr (see Example 6). The obtained transformant was designated as the strain with adhP. Also, *E. coli* Rosetta2 (DE3) (Novagen) was transformed using pRSF-Duet-NpAD-SeAR and pCDF-Duet-fd-fdr (see Example 6). The obtained transformant was designated as the strain without adhP.

The strain with adhP and the strain without adhP were inoculated into 15 mlf of LB medium (in 50-ml Falcon tubes) containing antibiotics (kanamycin 50 µg/ml, chloramphenicol 34 µg/ml, and streptomycin 10 µg/ml). These strains were inoculated from the glycerol stocks. Thereafter, culture was conducted at 37° C. and 180 rpm for 18 hours. Two each of the strains with adhP and the strains without adhP were subjected to culture. Thereafter, 30 ml of the culture solution was inoculated, and culture was further conducted in a 5-1 jar fermentor (Biott). In this case, culture was conducted in 2.5 l of 2×YT medium containing 0.01% TritonX-100 and the antibiotics. Culture was further conducted while regulating a pH to 7.2 with the use of a 5 N NaOH solution at an aeration rate of 0.4 vvm, an agitation rate of 300 rpm, and temperature of 37° C. Also, IPTG (final concentration: 0.5 mM) was added when O.D. 600 nm reached 0.6 to 0.9, the agitation rate was changed to 120 rpm, and temperature was changed to 30° C., and culture was then conducted for an additional 89 hours. Sampling was conducted 21, 41, 49, 65, and 72 hours after the initiation of culture, and a 40% glucose solution was added to a final concentration of 0.4%.

Figure 4:
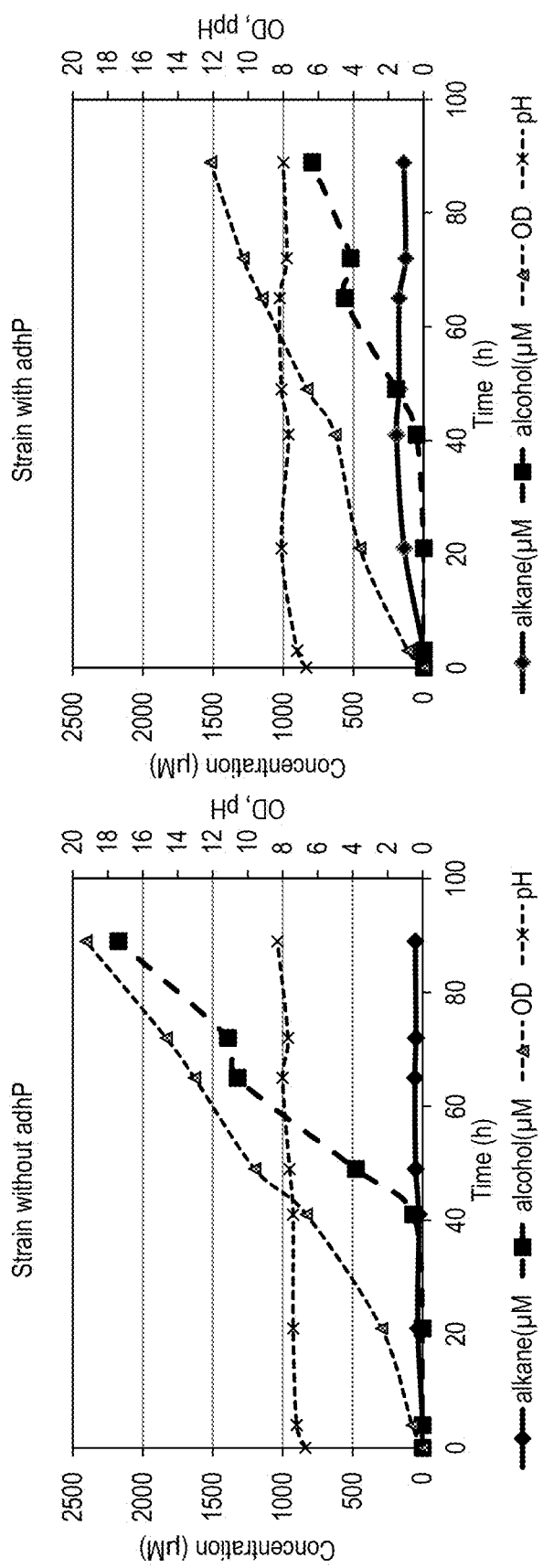
FIG. 4 shows a characteristic diagram demonstrating the results of measurements of an alkane and an alcohol generated with the elapse of the culture period concerning the strain with adhP (right) and the strain without adhP (left).
Figure 5:
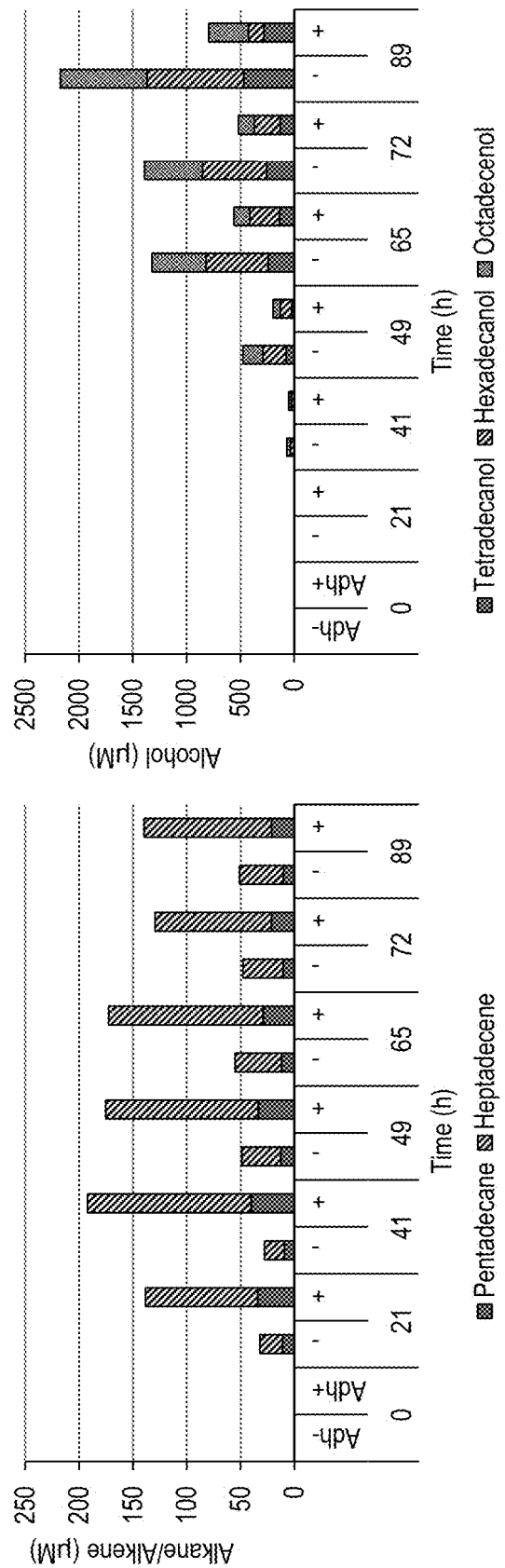
FIG. 5 shows a characteristic diagram demonstrating the results of analysis of the alkane component (left) and the alcohol component (right) generated with the elapse of the culture period concerning the strain with adhP and the strain without adhP.

During the culture, the alcohol concentration and the alkane concentration in the medium were measured via gas chromatography under the conditions described in Example 2 with the elapse of time. The results are shown in FIG. 4 and in FIG. 5. In FIG. 5, the strain with adhP is indicated as "Adh+" or simply as "+," and the strain without adhP is indicated as "Adh−" or simply as "−." As shown in FIG. 4 and in FIG. 5, the amount of an alcohol generated by the strain with adhP into which the adhP gene had been introduced was smaller than the amount thereof generated by the strain without adhP into which the adhP gene had not been introduced. That is, the amount of an alkane production was found to increase to a significant extent.

What is claimed is:

1. An expression vector encoding an aldehyde synthase comprising an aldehyde synthase gene and a regulatory region that regulates expression of such gene, wherein the aldehyde synthase gene comprises a nucleic acid sequence that has 85% or higher sequence identity to the nucleic acid sequence as shown in SEQ ID NO: 1 and further conserves encoding valine 36 and valine 322 and wherein the aldehyde synthase has activity for synthesizing an aldehyde from an alcohol.

2. A purified aldehyde synthase encoded by the aldehyde synthase gene of the expression vector according to claim 1.

3. An aldehyde synthase expressed by the expression vector according to claim 1, wherein the aldehyde synthase comprises an amino acid sequence as shown in SEQ ID NO: 2.

4. A recombinant microorganism prepared by introducing the expression vector according to claim 1 into a host microorganism.

5. The recombinant microorganism according to claim 4, wherein the host microorganism is a bacterium of *Escherichia coli* or *Klebsiella*.

6. The recombinant microorganism according to claim 4, which further comprises a decarbonylase gene, a ferredoxin gene, and a ferredoxin reductase gene introduced thereinto.

7. A method for producing an alkane comprising culturing the recombinant microorganism according to claim 4.

8. The method for producing an alkane according to claim 7, wherein the recombinant microorganism is cultured in an alkaline medium.

9. The method for producing an alkane according to claim 7, which further comprises recovering an alkane from a medium in which the recombinant microorganism is cultured.

10. The method for producing an alkane according to claim 7, which further comprises recovering an alkane from a medium in which the recombinant microorganism is cultured and purifying the recovered alkane.

11. The method for producing an alkane according to claim 7, which further comprises producing an alkane having 9 to 20 carbon atoms.

12. A method for producing an alkane comprising culturing the recombinant microorganism according to claim 5.

13. The method for producing an alkane according to claim 12, wherein the recombinant microorganism is cultured in an alkaline medium.

14. The method for producing an alkane according to claim 12, which further comprises recovering an alkane from a medium in which the recombinant microorganism is cultured.

15. The method for producing an alkane according to claim 12, which further comprises recovering an alkane from a medium in which the recombinant microorganism is cultured and purifying the recovered alkane.

16. The method for producing an alkane according to claim 12, which further comprises producing an alkane having 9 to 20 carbon atoms.

17. A method for producing an alkane comprising culturing the recombinant microorganism according to claim 6.

18. The method for producing an alkane according to claim 17, wherein the recombinant microorganism is cultured in an alkaline medium.

19. The method for producing an alkane according to claim 17, which further comprises recovering an alkane from a medium in which the recombinant microorganism is cultured.

20. The method for producing an alkane according to claim 17, which further comprises recovering an alkane from a medium in which the recombinant microorganism is cultured and purifying the recovered alkane.

* * * * *